(12) United States Patent
Ohki et al.

(10) Patent No.: US 8,236,813 B2
(45) Date of Patent: Aug. 7, 2012

(54) TRICYCLIC PYRAZOLOPYRIMIDINE DERIVATIVES

(75) Inventors: Hitoshi Ohki, Tokyo (JP); Tooru Okayama, Chiba (JP); Masahiro Ikeda, Tokyo (JP); Masahiro Ota, Tokyo (JP); Yoshihiro Shibata, Chiba (JP); Toshiyuki Nakanishi, Chiba (JP); Yasusi Ueda, Kanagawa (JP); Nobuyuki Suzuki, Kanagawa (JP); Shinji Matuura, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 12/915,982

(22) Filed: Oct. 29, 2010

(65) Prior Publication Data

US 2011/0071170 A1   Mar. 24, 2011

Related U.S. Application Data

(63) Continuation of application No. PCT/JP2010/052855, filed on Feb. 24, 2010.

(30) Foreign Application Priority Data

Feb. 25, 2009   (JP) ................. 2009-042963

(51) Int. Cl.
*C07D 491/00* (2006.01)
*C07D 239/00* (2006.01)
*C07D 471/00* (2006.01)
*C07D 487/00* (2006.01)
*A01N 43/54* (2006.01)
*A61K 31/505* (2006.01)

(52) U.S. Cl. ........................ 514/267; 544/251
(58) Field of Classification Search ................... 514/267; 544/251
See application file for complete search history.

(56) References Cited

U.S. PATENT DOCUMENTS

2010/0113410 A1* 5/2010 Ohsuki et al. ............ 514/210.18

FOREIGN PATENT DOCUMENTS

| WO | 98/43991 A1 | 10/1998 |
|---|---|---|
| WO | 2004/047755 A2 | 6/2004 |
| WO | 2005/028434 A2 | 3/2005 |
| WO | 2006/015263 A2 | 2/2006 |
| WO | 2008/035629 A1 | 3/2008 |
| WO | 2008/049105 A2 | 4/2008 |
| WO | 2008/093075 A2 | 8/2008 |
| WO | 2008/100447 A2 | 8/2008 |
| WO | 2005/021568 A2 | 5/2009 |

OTHER PUBLICATIONS

Akashi, S., "Investigation of Molecular Interaction Within Biological Macromolecular Complexes by Mass Spectrometry," Medicinal Research Reviews 26(3):339-368, May 2006.
Blagg, B.S.J., and T.D. Kerr, "Hsp90 Inhibitors: Small Molecules That Transform the Hsp90 Protein Folding Machinery Into a Catalyst for Protein Degradation," Medicinal Research Reviews 26(3):310-338, May 2006.
Calderwood, S.K., et al., "Heat Shock Proteins in Cancer: Chaperones of Tumorigenesis," Trends in Biochemical Sciences 31(3):164-172, Mar. 2006.
Dymock, B.W., et al., "Novel, Potent Small-Molecule Inhibitors of the Molecular Chaperone Hsp90 Discovered Through Structure-Based Design," Journal of Medicinal Chemistry 48(13):4212-4215, Jun. 2005.
Hammond, D.M., et al., "The Syntheses of Tricyclic Analogues of O6-Methylguanine," Organic & Biomolecular Chemistry 1(23):4166-4172, Dec. 2003.
He, H., et al., "Identification of Potent Water Soluble Purine-Scaffold Inhibitors of the Heat Shock Protein 90," Journal of Medicinal Chemistry 49(1):381-390, Jan. 2006.
Hornillo-Araujo, A.R., et al., "The Syntheses and Properties of Tricyclic Pyrrolo[2,3-d]pyrimidine Analogues of S6-Methylthioguanine and O6-Methylguanine," Organic & Biomolecular Chemistry 4(9):1723-1729, 2006.
Kamal, A., et al., "Therapeutic and Diagnostic Implications of Hsp90 Activation," Trends in Molecular Medicine 10(6):283-290, Jun. 2004.
Sōti, C., et al., "Heat Shock Proteins as Emerging Therapeutic Targets," British Journal of Pharmacology 146(6):769-780, Nov. 2005.

* cited by examiner

*Primary Examiner* — Noble Jarrell
*Assistant Examiner* — Erich A Leeser
(74) *Attorney, Agent, or Firm* — Christensen O'Connor Johnson Kindness PLLC

(57) ABSTRACT

A pyrazolopyrimidine compound represented by formula (1) that inhibits the function of HSP90 as a chaperone protein and that has antitumor activity, a medicament comprising a compound represented by formula (1), a pharmaceutical composition comprising a compound represented by formula (1), and a method for treating cancer using a compound represented by formula (1).

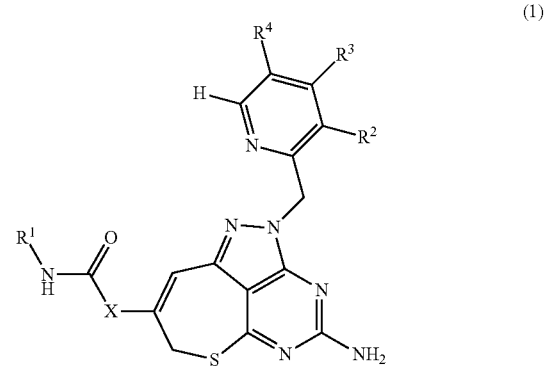

(1)

41 Claims, No Drawings

TRICYCLIC PYRAZOLOPYRIMIDINE DERIVATIVES

CROSS REFERENCES TO RELATED APPLICATIONS

This application is a continuation of International Application No. PCT/JP2010/052855, filed Feb. 24, 2010, which claims priority from Japanese Application No. 2009-042963, filed Feb. 29, 2006. Each application is expressly incorporated herein by reference in its entirety.

TECHNICAL FIELD

The present invention relates to a compound having a tricyclic pyrazolopyrimidine skeleton which inhibits the effect of heat shock protein 90 (HSP90).

BACKGROUND ART

HSP90 is a major intracellular chaperone protein. Chaperone proteins are proteins that bind to various proteins to assist in folding of the bound proteins. A group of proteins whose folding requires HSP90 are generally called HSP90 client proteins.

It is assumed that HSP90 as well as multiple proteins such as co-chaperones, partner proteins and immunophilins are involved in the mechanism of folding of client proteins by HSP90 and that they collaboratively assist in folding of HSP90 client proteins (Non Patent Document 1); however, the details of the mechanism are still not sufficiently clear.

It is assumed that HSP90 client proteins form a complex with HSP90, co-chaperones and the like and are then conformationally changed to mature proteins and that the proteins are ubiquitinated and degraded by proteasomes when they are not folded normally by HSP90 and the like (Non Patent Documents 1 to 4).

In recent years, HSP90 inhibitors have been expected as candidates for therapeutic agents for various diseases (for example, cancer, neurodegenerative diseases such as Alzheimer's disease, cardiovascular diseases, infections, autoimmune diseases, and diseases associated with apoptotic cell injury) (Non Patent Document 2).

In particular, since many cancer-associated proteins including molecular targets for anticancer agents are HSP90 client proteins, HSP90 inhibitors have been expected as candidates for anticancer agents. For example, multiple proteins involved in the occurrence and development of cancer such as Her2, Raf, Akt and telomerase are known as HSP90 client proteins (Non Patent Document 1). It is assumed that these cancer-associated proteins are changed from immature proteins to mature proteins and act to cause malignant transformation of cells, respectively, by use of HSP90 as a chaperone protein. HSP90 is a protein that exists not only in cancer cells but also in normal cells, and it is reported that the affinity with a client protein and the ATPase activity necessary for its chaperone activity are higher in cancer cells than in normal cells (Non Patent Documents 1 to 3). Therefore, HSP90 inhibitors are assumed to be capable of inactivating multiple cancer-associated proteins simultaneously in a cancer cell-specific manner, and have been expected as candidates for anticancer agents that are potent and have a broad antitumor spectrum.

Geldanamycin, herbimycin, 17-allylaminogeldanamycin (17-AAG) and the like are conventionally known as HSP90 inhibitors (Non Patent Documents 1 to 4). These compounds bind to the ATP binding pocket at the N-terminal of HSP90 and inhibit binding of HSP90 to ATP in order to inhibit the function of HSP90 as a chaperone protein. Various compounds inhibiting HSP90 are reported in addition to the above compounds (Patent Document 1, Patent Document 2, Patent Document 3, Non Patent Document 5 and Non Patent Document 6) and a tricyclic pyrazolopyrimidine derivative is also reported (Patent Document 4).

Moreover, several publications have reported the intended uses of tricyclic pyrazolopyrimidine derivatives and compounds having a condensed ring structure, which also have three constituent heterocyclic rings, for anticancer purposes (Patent Documents 5 to 9, and Non Patent Documents 7 and 8).

Citation List

Patent Documents

Patent Document 1: WO 2005/28434

Patent Document 2: WO 2008/049105

Patent Document 3: WO 2008/093075

Patent Document 4: WO 2008/035629

Patent Document 5: WO 2004/047755

Patent Document 6: WO 2006/015263

Patent Document 7: WO 2005/021568

Patent Document 8: WO 1998/043991

Patent Document 9: WO 2008/100447

Non Patent Documents:

Non Patent Document 1: Medicinal Research Reviews (2006) Vol. 26, No. 3, 310-338

Non Patent Document 2: TRENDS in Molecular Medicine (2004) Vol. 10, No. 6, 283-290

Non Patent Document 3: British Journal of Pharmacology (2005) 146, 769-780

Non Patent Document 4: TRENDS in Biochemical Sciences (2006) March, 31 (3), 164-172

Non Patent Document 5: Journal of Medicinal Chemistry (2005) Vol. 48, No. 13, 4212-4215

Non Patent Document 6: Journal of Medicinal Chemistry (2006) Vol. 49, No. 1, 381-390

Non Patent Document 7: Organic & Biomolecular Chemistry (2003) Vol. 1, No. 23, 4166-4172

Non Patent Document 8: Organic & Biomolecular Chemistry (2006) Vol. 4, No. 9, 1723-1729

SUMMARY OF INVENTION

Problem to be Solved by the Invention

Although HSP90 inhibitors have been expected to be used as medicaments, in particular as anticancer agents, no compounds have been actually used as medicaments so far.

Means for Solving the Problem

As a result of extensive studies to solve the above problems, the present inventors have found a novel compound that inhibits the ATPase activity of HSP90 and has antitumor activity, which is represented by formula (1) as shown below, thereby completing the present invention. Moreover, the inventors have carried out in vivo antitumor activity tests, safety tests, metabolic stability tests, metabolic enzyme inhibition tests, etc., on the compound of the present invention. As a result, they have found that the compound of the present invention has various properties required for medicaments.

More specifically, the present invention provides:
[1] A compound represented by the formula (1) or a salt thereof:

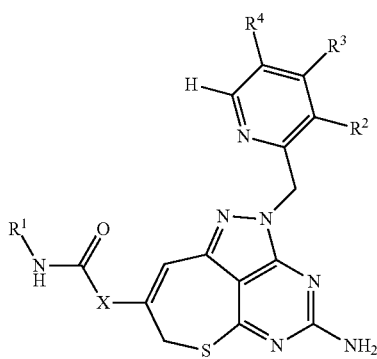

(1)

wherein, in formula (1),
R¹ represents a $C_1$-$C_6$ alkyl group which may be substituted by 1 to 3 halogen atoms, or a hydrogen atom,
R² represents a halogen atom,
R³ represents a $C_1$-$C_6$ alkyl group or a $C_1$-$C_6$ alkoxy group,
R⁴ represents a $C_1$-$C_6$ alkyl group which may be substituted by 1 to 3 halogen atoms, a cyano group, a halogen atom, or a hydrogen atom, and
X represents a single bond or a methylene group.
[2] 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide.
[3] 2-{4-amino-2-[(3-bromo-4-methoxy-5-methylpyridin-2-yl)methyl]-2,7-dihydro-6-thia-1,2,3,5-tetraazabenzo[cd]azulen-8-yl}-N-methylacetamide.
[4] 2-{4-amino-2-[(3-bromo-4-methoxy-5-methylpyridin-2-yl)methyl]-2,7-dihydro-6-thia-1,2,3,5-tetraazabenzo[cd]azulen-8-yl}acetamide.
[5] 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-(2-fluoroethyl)acetamide.
[6] 4-amino-2-[(3-chloro-4-methoxypyridin-2-yl)methyl]-N-(2,2-difluoroethyl)-2,7-dihydro-6-thia-1,2,3,5-tetraazabenzo[cd]azulen-8-carboxamide.
[7] A hydrobromide of a compound according to any one of [2] to [6].
[8] A hydrochloride of a compound according to any one of [2] to [6].
[9] A methanesulfonate of a compound according to any one of [2] to [6].
[10] An ethane-1,2-disulfonate of a compound according to any one of [2] to [6].
[11] An HSP90 inhibitor comprising a compound according to any one of [1] to [10] or a salt thereof.
[12] An agent for inhibiting the ATPase activity of HSP90, which comprises a compound according to any one of [1] to [10] or a salt thereof.
[13] An agent for inhibiting the binding of HSP90 to ATP, which comprises a compound according to any one of [1] to [10] or a salt thereof.
[14] A medicament, which comprises a compound according to any one of [1] to [10] or a salt thereof as an active ingredient.
[15] An anticancer agent, which comprises a compound according to any one of [1] to [10] or a salt thereof as an active ingredient.
[16] A pharmaceutical composition, which comprises a compound according to any one of [1] to [10] or a salt thereof and a pharmacologically acceptable carrier.
[17] A method for treating cancer, which comprises administering a compound according to any one of [1] to [10] or a salt thereof.
[18] Use of a compound according to any one of [1] to [10] or a salt thereof for the manufacture of a medicament.
[19] An anticancer agent according to [15], wherein the cancer involves the excessive expression of an HSP90 client protein(s).
[20] A method for treating cancer according to [17], wherein the cancer involves the excessive expression of an HSP90 client protein(s).
[21] An anticancer agent according to [15], wherein the cancer involves the mutation of an HSP90 client protein.
[22] A method for treating cancer according to [17], wherein the cancer involves the mutation of an HSP90 client protein(s).
[23] An anticancer agent according to [15], wherein the cancer involves the activation of an HSP90 client protein(s).
[24] A method for treating cancer according to [17], wherein the cancer involves the activation of an HSP90 client protein(s).
[25] An anticancer agent according to [15], wherein the cancer involves the activation of an intracellular signalling pathway, to which an HSP90 client protein(s) belongs.
[26] A method for treating cancer according to [17], wherein the cancer involves the activation of an intracellular signalling pathway, to which an HSP90 client protein(s) belongs.
[27] An anticancer agent according to [15], wherein the cancer is dependent on an HSP90 client protein(s).
[28] A method for treating cancer according to [17], wherein the cancer is dependent on an HSP90 client protein(s).

Advantages of the Invention

According to the present invention, there is provided a novel pyrazolopyrimidine derivative having HSP90 inhibitory activity, which is represented by the above formula (1). The compound of the present invention is useful as an anti-tumor agent.

DESCRIPTION OF EMBODIMENTS

In the present invention, "heat shock protein 90" or "HSP90" refers to any or all of the HSP90 family unless otherwise specified. The HSP90 family includes HSP90α, HSP90β, 94 kDa glucose-regulated protein (GRP94) and Hsp75/tumor necrosis factor receptor associated protein 1 (TRAP1), for example.

In the present invention, "HSP90 inhibitor" refers to a compound or composition that partially or completely inhibits an effect of HSP90. Examples of the HSP90 inhibitor include a compound or composition that partially or completely inhibits the expression of HSP90 and a compound or composition that partially or completely inhibits the function of HSP90 as a chaperone protein.

Here, "function of HSP90 as a chaperone protein" refers to a function of HSP90 to assist folding of a client protein to convert the client protein to its functioning form, or a function of HSP90 to stabilize a client protein, for example.

Accordingly, specific examples of the HSP90 inhibitor include a compound inhibiting the expression of HSP90, a compound inhibiting binding of HSP90 to a client protein, a compound inhibiting binding of HSP90 to co-chaperones or immunophilins, a compound inhibiting binding of HSP90 to ATP, a compound inhibiting the ATPase activity of HSP90 and a compound inhibiting the conformational change of HSP90. The HSP90 inhibitor can be used as a therapeutic agent for a disease caused by an effect of HSP90.

Examples of an HSP90 client protein include: growth factor receptor kinases such as Her2, EGFR, c-Kit, c-Met, KDR, Flt3, IGF-1R, and PDGF; intracellular kinases such as PDK1, Akt, Raf, S6, Cdk4, Cdk6, Chk1, PLK1, Src, Aurora B, Bcr-Abl, GSK3β and ERK5; steroid receptors such as GR, ERα, PR, and AR; and others such as HIF-1, Survivin, Tert, Bcl-6, and p53.

In the present invention, examples of the "disease caused by an effect of HSP90" include cancer, neurodegenerative diseases such as Alzheimer's disease, cardiovascular diseases, infections, autoimmune diseases, and diseases associated with apoptotic cell injury. In the present invention, the terms "tumor" and "cancer" can be used exchangeably. Further, in the present invention, tumor, malignant tumor, cancer, malignant neoplasm, carcinoma, sarcoma, and the like may be generically referred to as "tumor" or "cancer".

Individual substituents in the formula (1) of the $R^1$ represents a $C_1$-$C_6$ alkyl group which may be substituted by 1 to 3 halogen atoms, or a hydrogen atom.

Herein, the "$C_1$-$C_6$ alkyl group which may be substituted by 1 to 3 halogen atoms" refers to a linear, branched, or cyclic alkyl group having 1 to 6 carbon atoms, which is unsubstituted or is substituted by 1 to 3 halogen atoms. Examples of such an alkyl group having 1 to 6 carbon atoms include a methyl group, an ethyl group, a propyl group, an isopropyl group, a cyclopropyl group, a cyclobutyl group, a cyclopentyl group and a cyclohexylethyl group. Examples of a halogen atom substitutent for such an alkyl group include a fluorine atom, a chlorine atom, a bromine atom and an iodine atom. Such a substituent may be positioned on any carbon atom of the alkyl group. When the alkyl group has multiple substituents, the substituents may be on the same carbon or different carbons. Such a halogen atom substituent for the alkyl group is preferably a fluorine atom or a bromine atom, and more preferably a fluorine atom.

$R^1$ is preferably an unsubstituted $C_1$-$C_3$ alkyl group, a $C_1$-$C_3$ alkyl group having a fluorine atom as a substituent, or a hydrogen atom, and more preferably a methyl group, an ethyl group, a fluoroethyl group, a difluoroethyl group, or a hydrogen atom.

$R^2$ represents a halogen atom. Examples of such a halogen atom include a fluorine atom, a chlorine atom, a bromine atom and an iodine atom.

$R^2$ is preferably a fluorine atom, a chlorine atom or a bromine atom, and more preferably a chlorine atom or a bromine atom.

$R^3$ represents a $C_1$-$C_6$ alkyl group or a $C_1$-$C_6$ alkoxy group.

Herein, the "$C_1$-$C_6$ alkyl group" has the same definitions as those in $R^2$ above. The "$C_1$-$C_6$ alkoxy group" refers to a $C_1$-$C_6$ alkoxy group having the above described "$C_1$-$C_6$ alkyl group" as an alkyl portion thereof.

$R^3$ is preferably a $C_1$-$C_3$ alkyl group or a $C_1$-$C_3$ alkoxy group, and more preferably a methyl group, an ethyl group or a methoxy group.

$R^4$ represents a $C_1$-$C_6$ alkyl group which may be substituted by 1 to 3 halogen atoms, a cyano group, a halogen atom, or a hydrogen atom.

Herein, the "$C_1$-$C_6$ alkyl group which may be substituted by 1 to 3 halogen atoms" has the same definitions as those in $R^2$ above.

$R^4$ is preferably a $C_1$-$C_3$ alkyl group, a cyano group, a fluorine atom or a hydrogen atom.

X is preferably a single bond or a methylene group.

The compound represented by formula (1) according to the present invention may be present as a stereoisomer or an optical isomer derived from an asymmetric carbon atom. The stereoisomer, the optical isomer and a mixture thereof are all included in the present invention.

The compound represented by formula (1) according to the present invention is particularly preferably any one compound selected from the following group:

2-{4-amino-2-[(3-chloro-4-methoxy-5-methylpyridin-2-yl) methyl]-2,7-dihydro-6-thia-1,2,3,5-tetraazabenzo[cd] azulen-8-yl}-N-methylacetamide;

2-{4-amino-2-[(3-bromo-4-methoxy-5-methylpyridin-2-yl) methyl]-2,7-dihydro-6-thia-1,2,3,5-tetraazabenzo[cd] azulen-8-yl}-N-methylacetamide;

2-{4-amino-2-[(3-bromo-4-methoxy-5-methylpyridin-2-yl) methyl]-2,7-dihydro-6-thia-1,2,3,5-tetraazabenzo[cd] azulen-8-yl}acetamide;

2-{4-amino-2-[(3-chloro-4-methoxy-5-methylpyridin-2-yl) methyl]-2,7-dihydro-6-thia-1,2,3,5-tetraazabenzo[cd] azulen-8-yl}-N-(2-fluoroethyl)acetamide; and 4-amino-2-[(3-chloro-4-methoxypyridin-2-yl)methyl]-N-(2, 2-difluoroethyl)-2,7-dihydro-6-thia-1,2,3,5-tetraazabenzo [cd]azulen-8-carboxamide.

The compound represented by formula (1) according to the present invention can be converted to a pharmacologically acceptable salt, as desired. Examples of such salts include: halogenated hydroacid salts such as hydrochloride or hydroiodide salts; inorganic acid salts such as nitrates, perchlorates, sulfates and phosphates; lower alkanesulfonates such as methanesulfonates, trifluoromethanesulfonates or ethanesulfonates; arylsulfonates such as benzenesulfonates or p-toluenesulfonates; organic acid salts such as formates, acetates, malates, fumarates, succinates, citrates, tartrates, oxalates or maleates; and amino acid salts such as ornithinates, glutamates or aspartates. Of these, halogenated hydroacid salts and organic acid salts are preferable, and bromate, hydrochloride, methanesulfonate or ethane-1,2-disulfonate is more preferred.

The compound represented by formula (1) according to the present invention or a salt thereof may be present in the form of a free form, or in the form of a hydrate or a solvate. It may be present in the free form, or in the form of a hydrate salt or the like, as a result of the absorption of moisture from the air. The type of solvate is not particularly limited, as long as it is pharmacologically acceptable. Specifically, a hydrate, an ethanolate or the like is preferred. Moreover, when a nitrogen atom is present in the compound represented by the formula (1) according to the present invention, it may be an N-oxide form. Such solvate, hydrate, hydrate salt, and N-oxide forms are also included in the scope of the present invention.

Depending on the types of substituents or the combination thereof, the compound represented by formula (1) according to the present invention may be present as various types of isomers including geometric isomers such as a cis isomer or a trans isomer, tautomers, or optical isomers such as a d-form or an l-form. The compound of the present invention includes all of those isomers, stereoisomers, and mixtures of such isomers and stereoisomers that are mixed at any given ratios, unless otherwise specified.

The compound represented by the formula (1) according to the present invention may also comprise an atomic isotope(s) of one or more constituent atoms thereof in a nonnatural ratio. Examples of such an atomic isotope include deuterium ($^2$H), tritium ($^3$H), iodine-125 ($^{125}$I) and carbon-14 ($^{14}$C). These compounds are useful as therapeutic or preventive agents, or reagents used for studies such as assay reagents, and diagnostic agents such as in vivo image diagnostic agents. Regardless of whether or not they are radioactive compounds, all isotopic variants of the compound represented by formula (1) are included in the scope of the present invention.

Moreover, the present invention also includes a compound that is converted to a compound (1) as an active ingredient of a pharmaceutical composition of the present invention as a result of a reaction with an enzyme, gastric acid or the like under physiological conditions in vivo; namely, a compound that is converted to the compound (1) as a result of enzymatic oxidation, reduction, hydrolysis or the like, or a "pharmacologically acceptable prodrug compound" that is converted to the compound (1) as a result of hydrolysis or the like due to gastric acid, etc.

Examples of the aforementioned prodrug include compounds obtained by acylation, alkylation, or phosphorylation of the amino group of the compound (1) (for example, compounds obtained by converting the above-mentioned amino group to eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl or tert-butyl, and other compounds).

A prodrug of the compound of the present invention can be produced from the compound (1) according to a known method. In addition, a prodrug of the compound of the present invention includes a prodrug that is converted to the compound (1) under physiological conditions, as described on pages 163-198 of "*Iyakuhin no Kaihatsu* (Development of Medicaments)" Vol. 7, *Bunshi Sekkei* (Molecular Design), Hirokawa Shoten Co., 1990.

Next, a typical method for producing the compound represented by the formula (1) will be described. It is to be noted that an appropriate protecting group may be used in each reaction, as necessary, or that a desired conversion may be performed in a common organic chemical reaction. The type of protecting group and the order of conversion of respective substituents are not particularly limited.

[Main Step 1]

A method for producing a compound represented by the formula (1), wherein X is a methylene group, will be described.

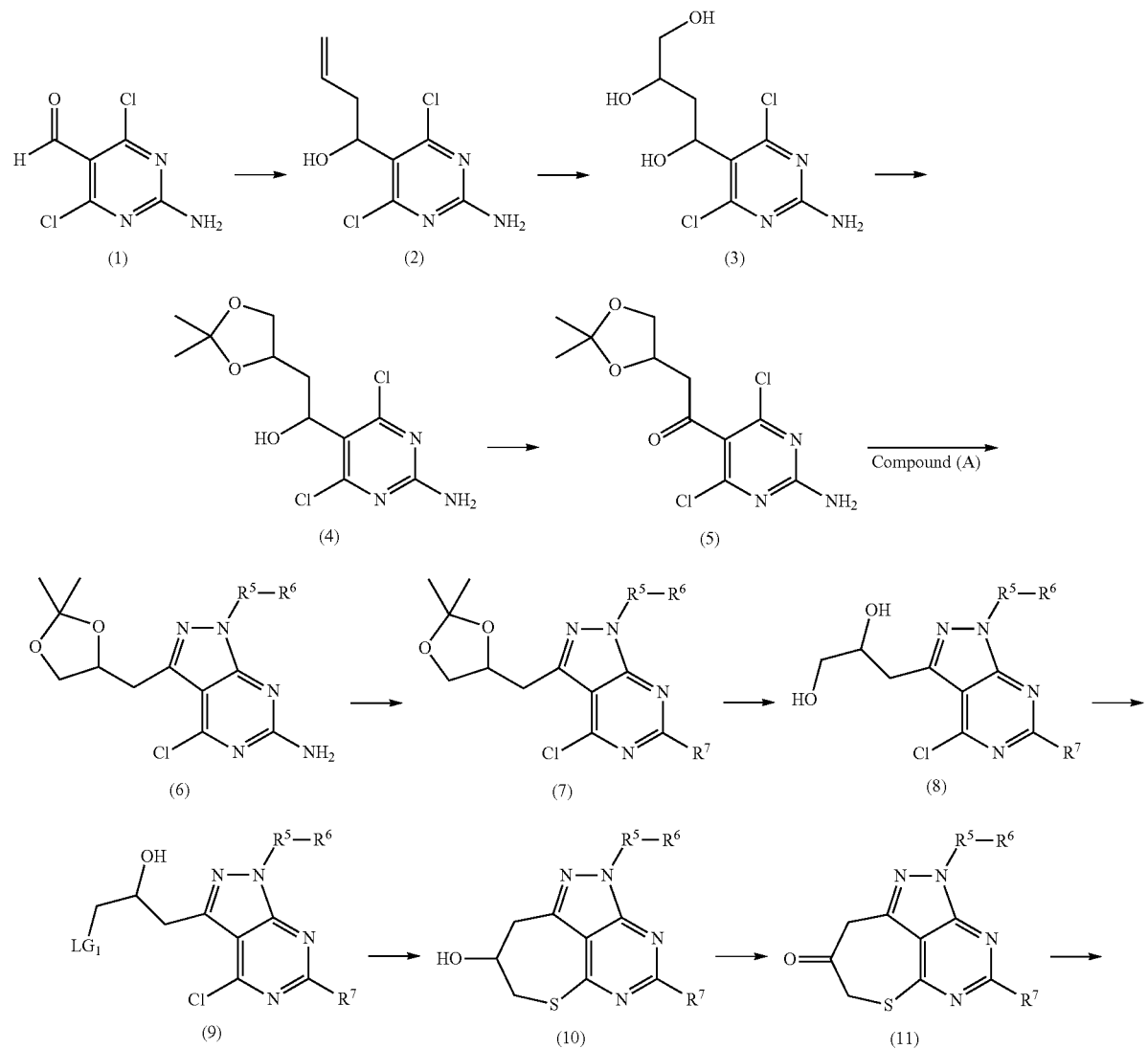

Scheme 1

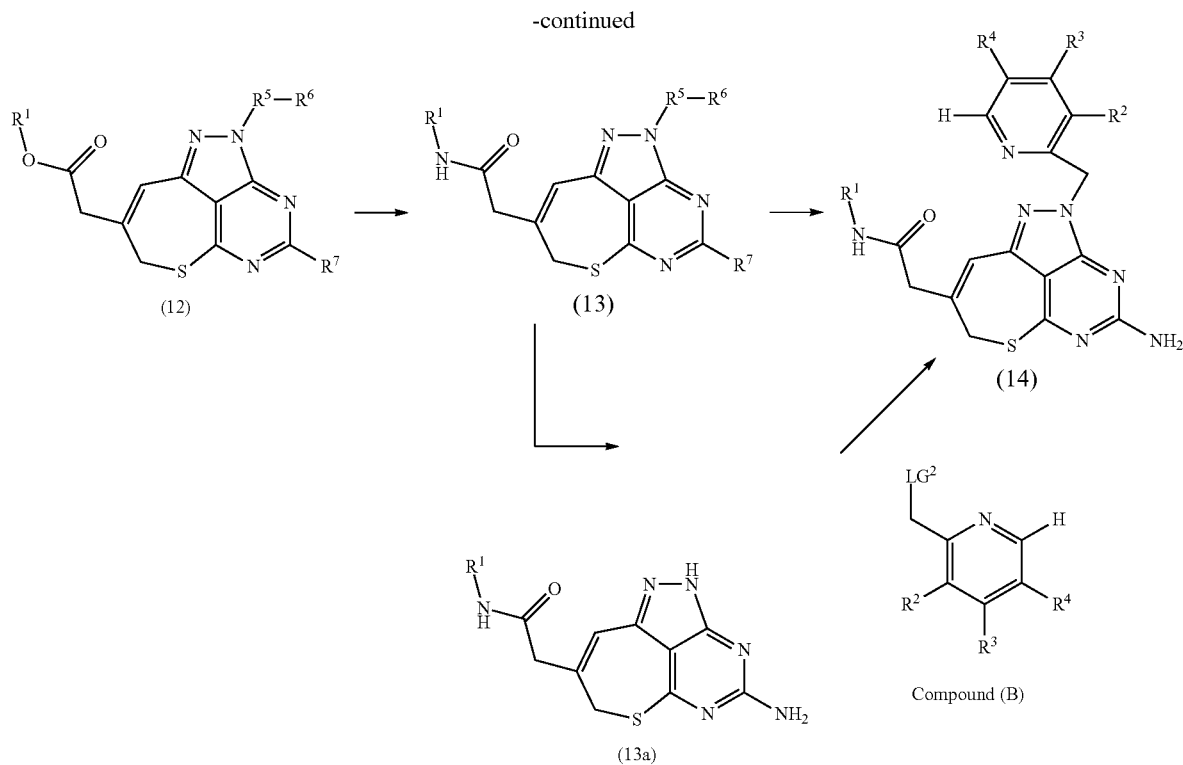

wherein $R^1$, $R^2$, $R^3$ and $R^4$ are as defined above, respectively, $R^5$ represents a methylene group which may be substituted by 1 or 2 alkyl groups having 1 to 6 carbon atoms, $R^6$ represents an aryl group which may have a substituent(s) or a heterocyclic group which may have a substituent(s), $R^7$ represents an amino group having a protecting group, and $LG^1$ and $LG^2$ each represent a leaving group. The leaving groups, $LG^1$ and $LG^2$, include a halogen atom, a toluenesulfonyloxy group, a methanesulfonyloxy group, a trifluoromethanesulfonyloxy group and the like. Protecting groups for the amino group include a benzyloxycarbonyl group, a tert-butoxycarbonyl group, a benzyl group and the like.

An aldehyde derivative (1) (obtainable as a commercially available product) is treated with allyl bromide and indium powders in a solvent to obtain a compound (2). The alkene derivative (2) can also be obtained using the aldehyde derivative (1) and a Grignard reagent such as allyl magnesium bromide. As a solvent, N,N-dimethylformamide, N-methylpyrrolidone, tetrahydrofuran, dimethyl sulfoxide or the like is preferred. The reaction temperature is preferably between −70° C. and 100° C., and more preferably between −20° C. and 50° C. The reaction time is preferably between 1 hour and 48 hours.

The alkene derivative (2) is subjected to a 1,2-dihydroxylation, so as to obtain a triol derivative (3). Examples of such dihydroxylation of an alkene include a reaction using potassium permanganate, a water addition reaction in the presence of mercury salt (Kucherov-Deniges method), an osmium oxidation reaction using a catalytic amount of osmium tetroxide and an amine oxide as a co-oxidant, and a dihydroxylation reaction using iodine (Prevoat method or Woodward method). Examples of solvents used in these reactions include N,N-dimethylformamide, N-methylpyrrolidone, tetrahydrofuran, dimethyl sulfoxide, methylene chloride, acetone, t-butanol, water and mixtures thereof. The reaction temperature is suitably between 0° C. and 100° C., and preferably between 10° C. and 50° C. The reaction time is preferably between 1 hour and 72 hours.

The triol derivative (3) can be converted to an acetal derivative (4) by treatment with 2,2-dimethoxypropane and a catalytic amount of an acid in a solvent such as N,N-dimethylformamide, N-methylpyrrolidone, tetrahydrofuran or dimethyl sulfoxide, or by treatment with such an acid catalyst in acetone. Examples of such an acid catalyst include Lewis acids including p-toluenesulfonic acid, hydrochloric acid, sulfuric acid and zinc chloride as typical examples. The reaction temperature is preferably between 0° C. and 100° C., and more preferably between 10° C. and 50° C. The reaction time is preferably between 1 hour and 48 hours.

Compound (4) can be converted to a ketone derivative (5) by treatment under appropriate oxidation reaction conditions. Examples of an oxidation reaction in this case include Mukaiyama oxidation for activating dimethyl sulfoxide or the like; Swern oxidation or an oxidation reaction using as its modification dicyclohexylcarbodiimide, trifluoroacetic anhydride, acetic anhydride or a sulfur trioxide-pyridine complex instead of oxalyl chloride; and an oxidation reaction using manganese dioxide. Examples of a solvent used herein include dioxane, tetrahydrofuran, and methylene chloride. The reaction temperature is preferably between −70° C. and 50° C. The reaction time is preferably between 1 hour and 48 hours.

The ketone derivative (5) can be converted to a compound (6) by treatment with a hydrazine derivative ($R^6$—$R^5$—$NHNH_2$) (compound (A)) in a solvent. Compound (A) can be produced by the method described in J. Am. Chem. Soc. 1995, 117, 4228-4239, etc. Examples of the solvent used in this reaction include alcohol, methylene chloride, tetrahydrofuran, dioxane and mixtures thereof. The reaction temperature is preferably between −20° C. and 50° C., and more preferably between 0° C. and 30° C. When compound (A) is replaced with its salt, an equivalent or excess of a base relative to the salt may suitably be used. An example of the base is triethylamine. The reaction time is preferably between 1 hour and 48 hours.

A diol derivative (8) can be obtained by protecting the amino group at the 6-position of compound (6) with an appropriate protecting group such as a benzyloxycarbonyl group or a tert-butoxycarbonyl group to convert it to a compound (7), and then treating the acetal derivative (7) with an acid such as sulfuric acid, hydrochloric acid or acetic acid. Examples of the solvent used in this reaction include alcohol, water, dioxane and mixtures thereof. The reaction temperature is preferably between −10° C. and 70° C., and more preferably between 0° C. and 40° C. The reaction time is preferably between 1 hour and 48 hours.

Compound (9) can be obtained by converting the hydroxyl group of compound (8) to a leaving group $LG^1$ such as a halogen atom, a toluenesulfonyloxy group, a methanesulfonyloxy group or a trifluoromethanesulfonyloxy group by treatment with thionyl chloride, thionyl bromide, toluenesulfonyl chloride, methanesulfonyl chloride or trifluoromethanesulfonyl chloride in the presence of a base, for example, based on common knowledge in organic chemistry. The reaction temperature is preferably between −78° C. and 30° C., and more preferably between −20° C. and 10° C. The reaction time is preferably between 1 hour and 48 hours.

Compound (10) can be obtained by reacting compound (9) with sodium bisulfide in a solvent such as N,N-dimethylformamide and then treating with a base. Alternatively, compound (10) can also be obtained by reacting compound (9) with potassium thioacetate in a solvent such as N,N-dimethylformamide. Examples of the base include potassium carbonate and potassium bicarbonate. The base is preferably potassium carbonate. The reaction temperature is suitably between −30° C. and 100° C., and preferably between −10° C. and 70° C.

Examples of the method for conversion of the hydroxyl group to an oxo group (conversion of compound (10) to compound (11)) include Mukaiyama oxidation, and Swern oxidation or an oxidation reaction using as its modification DCC, trifluoroacetic anhydride, acetic anhydride or a sulfur trioxide-pyridine complex instead of oxalyl chloride. These methods are described in The Chemical Society of Japan (ed.), "*Jikken Kagaku Koza* (Courses in Experimental Chemistry), 4th edition, Vol. 23, *Yuki Gosei* (Organic Synthesis) V" (Maruzen Co., Ltd., 1992) or the like.

An acetic acid ester derivative (12) can be produced by a homologation, including as a typical example, Wittig reaction of each commercially available reagent selected in order to obtain a desired $R^1$ group with the ketone derivative (11). The homologation is preferably a known reaction, and may be one described in *Jikken Kagaku Koza* (Courses in Experimental Chemistry) (4th edition, Vol. 22, edited by The Chemical Society of Japan, Maruzen Co., Ltd.) "*Yuki Gosei* (Organic Synthesis) I: *Tankasuiso, Harogen Kagobutsu* (Hydrocarbons, Halogen Compounds)", pp. 57-69.

An acetic acid amide derivative (13) can be produced by allowing monoalkylamine to act directly on the acetic acid ester derivative (12) in alcohol, or by hydrolyzing the acetic acid ester derivative (12) to obtain an acetic acid derivative and then subjecting it to a condensation reaction with various types of amines (obtainable as commercially available products). The ester hydrolysis reaction is preferably a known alkali hydrolysis. A reference is *Jikken Kagaku Koza* (Courses in Experimental Chemistry) (4th edition, Vol. 22, edited by The Chemical Society of Japan, Maruzen Co., Ltd.) "*Yuki Gosei* (Organic Synthesis) IV: *San, Aminosan, Peputido* (Acids, Amino Acids, Peptides)", pp. 6-11. A method generally used as a peptide synthesis method may suitably be used in the condensation reaction with amines. Examples of the peptide synthesis method include an azide method, an acid chloride method, a DCC (dicyclohexylcarbodiimide) method, an active ester method, a carbonyldiimidazole method, a method using a water-soluble carbodiimide and a method using diethyl cyanophosphate. These methods are described in M. Bondansky, Y. S. Klausner and M. A. Ondetti, "Peptide Synthesis"(A Wiley-interscience publication, New York, 1976), G. R. Pettit, "Synthetic Peptides" (Elsevier Scientific Publication Company, New York, 1976), The Chemical Society of Japan (ed.), "*Jikken Kagaku Koza* (Courses in Experimental Chemistry), 4th edition, Vol. 22, *Yuki Gosei* (Organic Synthesis) IV" (Maruzen Co., Ltd., 1992) or the like. Examples of the solvent used in the condensation reaction with various types of amines include N,N-dimethylformamide, N-methylpyrrolidone, pyridine, chloroform, methylene chloride, tetrahydrofuran, dioxane, acetonitrile and mixtures thereof. The reaction temperature is suitably between −20° C. and 50° C., and preferably between −10° C. and 30° C.

Compound (13) can be converted to a compound (13a) by acid treatment, oxidation treatment or hydrolysis, and the subsequent treatment performed under deprotection reaction conditions suitable for the protecting group in the amino group having a protecting group ($R^4$), when its $R^6$—$R^5$— group is a protecting group such as a 4-methoxybenzyl group. A typical example of the deprotection reaction conditions suitable for the protecting group will be described below. For example, when the amino group substituted with a protecting group is an alkanoylamino group or an aroylamino group, the group can be converted to an amino group by hydrolysis using an aqueous solution of sodium hydroxide, potassium hydroxide, ammonia or the like. When the amino group substituted with a protecting group is a tert-butoxycarbonylamino group or a di-tert-butoxycarbonylamino group, the group can be converted to an amino group by treatment with an acid such as hydrochloric acid or trifluoroacetic acid.

Compound (13a) can be converted to a compound (14) by treatment with a pyridine derivative (compound (B)) prepared by the method described in J. Med. Chem. 1992, 35, 438-450, etc., in a solvent in the presence of a base. Examples of the solvent include N,N-dimethylformamide, N-methylpyrrolidone, tetrahydrofuran and dimethylsulfoxide. Examples of the base include sodium hydride, sodium ethoxide, potassium tert-butoxide, potassium hydroxide, potassium carbonate and cesium carbonate. The reaction temperature is suitably between 0° C. and 100° C. The reaction time is suitably between 1 and 48 hours.

On the other hand, when the $R^6$—$R^5$— group of compound (13) is not a protecting group but is a substituent of interest, compound (14) can be obtained by treating the amino group having a protecting group ($R^7$) under the above-mentioned deprotection reaction conditions.

[Main Step 2]

A method for producing a compound represented by formula (1), wherein X is a single bond, will be described.

Scheme 2

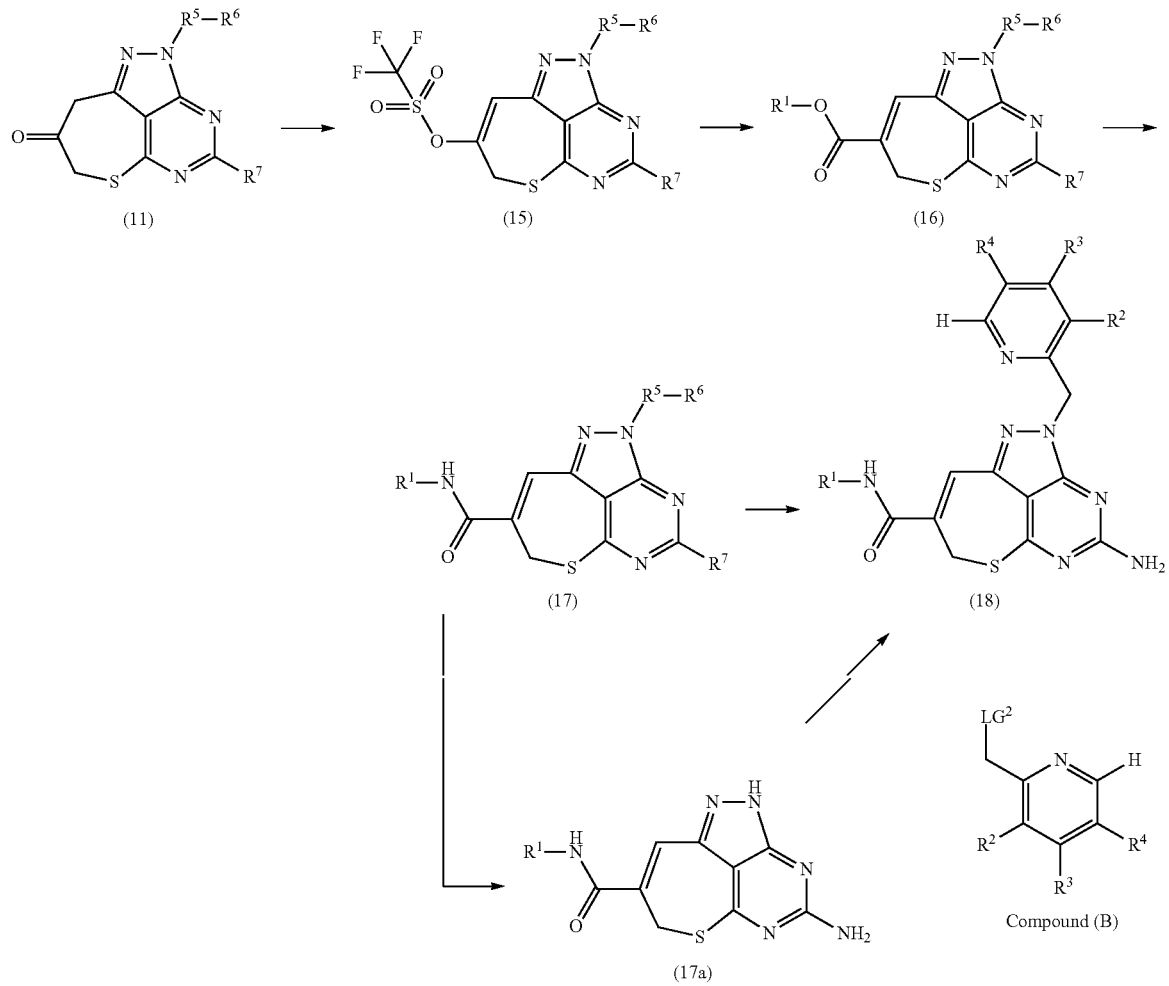

wherein R¹, R², R³, R⁴, R⁵, R⁶, R⁷ and LG² are as defined above, respectively.

A ketone derivative (11) can also be converted to a triflate compound (15) by treatment with trifluoromethanesulfonic anhydride in the presence of a base. Preferred examples of the solvent include methylene chloride, acetonitrile, tetrahydrofuran and N,N-dimethylformamide. The solvent is more preferably methylene chloride. Preferred examples of the base include sodium hydride, potassium hydride, sodium hydroxide, potassium hydroxide, potassium carbonate, sodium tert-butoxide, potassium tert-butoxide, pyridine, triethylamine, DBU and diisopropylethylamine. The base is more preferably triethylamine. The reaction temperature is preferably between −80° C. and 150° C., and more preferably between −10° C. and 40° C.

The triflate compound (15) can be converted to an ester form (16) by performing a coupling reaction with carbon monoxide in the presence of a metal catalyst and a base in alcohol. As such an alcohol, methanol and ethanol are preferred. The metal catalyst is preferably a palladium catalyst. Examples of the palladium catalyst include a [1,1′-bis(diphenylphosphino)ferrocene]dichloropalladium (II)/dichloromethane complex (1:1), dichlorobis(triphenylphosphine) palladium (II) and tetrakis(triphenylphosphine)palladium (0). The metal catalyst is preferably used in an amount of 0.01 to 0.2 molar equivalents relative to the triflate compound (15). Preferred examples of the base include inorganic bases such as tripotassium phosphate, potassium carbonate, sodium carbonate and cesium carbonate. The base is more preferably tripotassium phosphate, sodium carbonate or the like. The base is preferably used in an amount of 1 to 100 molar equivalents relative to the triflate compound (15). Examples of the additive include organophosphorus compounds such as 1,1′-bis(diphenylphosphino)ferrocene (dppf) and triphenylphosphine. The additive is preferably used in an amount of 0.05 to 0.2 molar equivalent relative to the triflate compound (15). The reaction temperature is preferably between −10° C. and the boiling point of the solvent, and more preferably between 0° C. and 100° C. The reaction time is generally between approximately 1 hour and 50 hours.

The subsequent step (the conversion of a compound (17) to a compound (18)) can be carried out by the same treatments in the method as shown in the above scheme 1 (the conversion of the compound (13) to the compound (14)).

Since the compound of the present invention or a salt thereof inhibits HSP90, it can be used as an HSP90 inhibitor, an agent for inhibiting the ATPase activity of HSP90, or an agent for inhibiting the binding of HSP90 to ATP. Thus, it can be used as a medicament comprising the compound of the present invention or a salt thereof, and particularly preferably as an anticancer agent.

The ATPase activity of HSP90 can be examined by an ATPase assay commonly used by a person skilled in the art. For example, the ATPase activity of HSP90 can be detected using a recombinant HSP90 protein and ATP in the presence or absence of the test compound, as described in Test Example 1 below. Alternatively, in an ATPase assay, the method described in Analytical Biochemistry 327, 176-183 (2004) or Nature 425, 407-410 (2003) may be suitably performed, for example.

Inhibition of the expression of HSP90 can be examined by Northern blotting, Western blotting, ELISA or the like commonly used by a person skilled in the art. For example, mRNA is recovered from cells cultured in the presence or absence of the test compound to perform Northern blotting. When the amount of HSP90 mRNA in mRNA recovered from the cells cultured in the presence of the test compound is reduced from that in mRNA recovered from the cells cultured in the absence of the test compound, the test compound is identified as a compound inhibiting the expression of HSP90. Alternatively, the amount of HSP90 protein may be suitably examined by performing Western blotting using the method described in Cancer. Res. 65, 6401-6408 (2005), for example.

Inhibition of binding of HSP90 to a client protein can be examined by immunoprecipitation and Western blotting commonly used by a person skilled in the art, for example. In immunoprecipitation and Western blotting, the method described in J. Biol. Chem. 277, 10346-10353 (2002) may be suitably performed, for example.

The compound inhibiting binding of HSP90 to co-chaperones or immunophilins can be examined by immunoprecipitation and Western blotting commonly used by a person skilled in the art, for example. Binding of HSP90 to co-chaperones or immunophilins may be suitably examined in the presence or absence of the test compound by performing the method described in Nature 425, 407-410 (2003), for example.

Inhibition of binding of HSP90 to ATP can be examined by a test for binding of labeled ATP to HSP90, for example. Binding of HSP90 to labeled ATP may be suitably examined in the presence or absence of the test compound by performing the method described in J. Biol. Chem. 272, 18608-18613 (1997), for example.

Inhibition of the conformational change of HSP90 can be examined by a conformational assay using bis-ANS (1,1'-bis (4-anilino-5-naphthalenesulfonic acid)), for example. In the conformational assay, the method described in J. Med. Chem. 47, 3865-3873 (2004) may be suitably performed, for example.

Cell growth inhibitory activity can be examined using a growth inhibition test method that is commonly used by a person skilled in the art. The cell growth inhibition activity can be determined by, for example, comparing the levels of cellular growth (for example, tumor cells) in the presence or absence of a test compound as described in the following Test Example 2.

The growth level can be examined using a test system for assaying living cells. Examples of the method for assaying living cells include a [$^3$H]-thymidine uptake test, a BrdU method and an MTT assay.

Moreover, in vivo antitumor activity can be examined using a method for testing antitumor activity commonly used by a person skilled in the art. For example, various types of tumor cells are transplanted into a mouse, a rat or the like, and after the confirmation of the survival of the transplanted cells, the compound of the present invention is administered to the animal via oral administration, intravenous administration, etc. Thereafter, several days to several weeks later, the growth of tumor in an agent non-administration group is compared with that in a compound administration group, so as to confirm the in vivo antitumor activity of the compound of the present invention.

The compound of the present invention can be used for treatment of tumors or cancers, such as lung cancer, gastrointestinal cancer, ovarian cancer, uterine cancer, breast cancer, liver cancer, head and neck cancer, blood cancer, renal cancer, testicular neoplasm, prostate cancer, multiple myeloma, skin cancer such as malignant melanoma, sarcoma, for example.

Since the compound of the present invention has HSP90 inhibitory action, it can be used for treatment of cancer in which HSP90 dependency is increased. Such cancers in which HSP90 dependency is increased include cancer that depends on an HSP90 client protein(s), cancer in which an HSP90 client protein(s) is excessively expressed, cancer in which an HSP90 client protein(s) is mutated, and the like. More specific examples include cancer in which Her2, c-Met, Flt3 or the like is excessively expressed, and cancer in which c-kit, PDGFR, Raf or the like is mutated. However, examples are not limited thereto.

Furthermore, many factor groups associated with cancer (RAS-MAPK, PI3K, telomerase, etc.) are present in an intracellular signalling pathway to which the HSP90 client protein belongs. If HSP90 is inhibited, signalling to such factors is also inhibited. As a result, the activation of the aforementioned intracellular signalling pathway is also inhibited. Thus, from this viewpoint as well, the compound of the present invention that is an HSP90 inhibitor can be preferably used for treatment of various types of cancers.

The pharmaceutical composition of the present invention comprises a compound of the present invention and a pharmacologically acceptable carrier. It can be used as various types of injections such as an intravenous injection, an intramuscular injection or a subcutaneous injection, or it can be administered by various methods such as oral administration or a percutaneous administration. The pharmacologically acceptable carrier refers to a pharmacologically acceptable material (for example, an excipient, a diluent, an additive, a solvent, etc.), which is associated with the transportation of the compound of the present invention or a composition comprising the compound of the present invention from a certain apparatus or organ to another apparatus or organ.

As a method for preparing a formulation, a suitable formulation (for example, an oral formulation or an injection) is selected, and a commonly used method for preparing various types of formulations can be applied depending on the administration method. Examples of oral formulations include tablets, powders, granules, capsules, pills, troches, solutions, syrups, elixirs, emulsions, and oily or aqueous suspensions. In the case of oral administration, the agent may be either a free form or a salt form. The aqueous formulation can be produced by forming an acid adduct with a pharmacologically acceptable acid or forming a salt of an alkali metal such as sodium. When the formulation is an injection, a stabilizer, a preservative, a solubilizer or the like can also be used in the formulation. The injection may be provided as a formulation to be prepared before use by storing a solution which may contain such an adjuvant or the like in a container and then converting it to a solid formulation by lyophilization or the like. One dose may be stored in one container, or multiple doses may be stored in one container.

Examples of solid formulations include tablets, powders, granules, capsules, pills and troches. These solid formulations may contain a pharmaceutically acceptable additive together with the compound of the present invention.

Examples of the additive include fillers, bulking agents, binders, disintegrants, solubilizers, wetting agents and lubricants. These can be selectively mixed as necessary to provide a formulation.

Examples of liquid formulations include solutions, syrups, elixirs, emulsions and suspensions. These liquid formulations may contain a pharmaceutically acceptable additive together with the compound of the present invention. Examples of the additive include suspending agents and emulsifiers. These can be selectively mixed as necessary to provide a formulation.

The compound of the present invention can be used for treating cancer of mammals, in particular humans. The dose and the dosage interval may be appropriately selected based on the judgment of the physician according to the site of disease and the body height, body weight, sex or medical history of the patient. When the compound of the present invention is administered to a human, the dose range is about 0.01 mg/kg body weight to about 500 mg/kg body weight, and preferably about 0.1 mg/kg body weight to about 100 mg/kg body weight per day. When the compound is administered to a human, the compound is preferably administered in one dose or two to four separate doses per day, and the administration is preferably repeated at appropriate intervals. The daily dose may exceed the aforementioned dose if necessary, based on the judgment of the physician.

The compound of the present invention may be used together with other antitumor agents. Examples of such other antitumor agents include an antitumor antibiotic, an antitumor plant ingredient, BRM (biological response modifier), hormone, vitamin, an antitumor antibody, a molecular-targeted agent, and other antitumor agents.

More specifically, examples of an alkylating agent include: alkylating agents such as nitrogen mustard, nitrogen mustard N-oxide, or chlorambucil; aziridine alkylating agents such as carboquone or thiotepa; epoxide alkylating agents such as dibromomannitol or dibromodulcitol; nitrosourea alkylating agents such as carmustine, lomustine, semustine, nimustine hydrochloride, streptozocin, chlorozotocin, or ranimustine; busulphan; improsulfan tosilate; and Dacarbazine.

Examples of various types of antimetabolites include: purine antimetabolites such as 6-mercaptopurine, 6-thioguanine, or thioinosine; pyrimidine antimetabolites such as fluorouracil, tegafur, tegafur-uracil, carmofur, doxifluridine, broxuridine, cytarabine, or enocitabine; and antifolics such as methotrexate or trimethotrexate.

Examples of an antitumor antibiotic include: anthracycline antibiotic antitumor agents such as mitomycin C, bleomycin, peplomycin, daunorubicin, aclarubicin, doxorubicin, pirarubicin, THP-adriamycin, 4'-epidoxorubicin, or epirubicin; chromomycin A3; and actinomycin D.

Examples of an antitumor plant ingredient include: vinca alkaloids such as vindesine, vincristine, or vinblastine; taxanes such as paclitaxel or docetaxel; and epipodophyllotoxins such as etoposide or teniposide.

Examples of a BRM include a tumor necrosis factor and indomethacin.

Examples of a hormone include hydrocortisone, dexamethasone, methylprednisolone, prednisolone, prasterone, betamethasone, triamcinolone, oxymetholone, nandrolone, methenolone, fosfestrol, ethinyl estradiol, chlormadinone, and medroxyprogesterone.

Examples of a vitamin include vitamin C and vitamin A.

Examples of an antitumor antibody and the molecular-targeted agent include trastuzumab, rituximab, cetuximab, nimotuzumab, denosumab, bevacizumab, infliximab, imatinib mesylate, gefitinib, erlotinib, sunitinib, lapatinib, and sorafenib.

Examples of other antitumor agents include cisplatin, carboplatin, oxaliplatin, tamoxifen, camptothecin, ifosfamide, cyclophosphamide, melphalan, L-asparaginase, aseclatone, schizophyllan, picibanil, procarbazine, pipobroman, neocarzinostatin, hydroxyurea, ubenimex, and krestin.

The present invention includes a method for preventing cancer and/or a method for treating cancer, which comprises the administration of a compound of the present invention or a salt thereof.

Further, the present invention also includes the use of a compound of the present invention, a salt thereof or a solvate thereof for the production of the aforementioned medicament.

The present invention will be specifically described with reference to Examples shown below; however, the present invention is not limited thereto, and they should not be construed as limitative in any sense. Reagents, solvents and starting materials not specifically described herein are readily available from commercial sources.

EXAMPLES

Example 1

(1) 1-(2-Amino-4,6-dichloropyrimidin-5-yl)-3-buten-1-ol

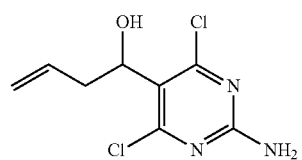

Indium powder (0.23 g) and zinc powder (1.31 g) were added to a mixture composed of commercially available 2-amino-4,6-dichloropyrimidine-5-carboaldehyde (1.92 g) and N,N-dimethylformamide (20 ml). Thereafter, sodium iodide (0.15 g) and allyl bromide (1.73 ml) were added to the mixture at room temperature. The resulting mixture was stirred for 3 hours. Thereafter, the reaction mixture was filtered through celite, and ethyl acetate was then added to the filtrate. The resulting mixture was successively washed with 1 N hydrochloric acid and a saturated saline in this order. The organic layer was dried over anhydrous sodium sulfate, and was then concentrated. Thereafter, hexane was added to the residue, and a precipitate was then collected by filtration, so as to obtain the above title compound (1.75 g) as a solid.

$^1$H-NMR (DMSO-D$_6$) δ: 2.55-2.69 (2H, m), 4.95-5.09 (3H, m), 5.37 (1H, d, J=4.1 Hz), 5.67-5.77 (1H, m), 7.42 (2H, s).

(2) 1-(2-Amino-4,6-dichloropyrimidin-5-yl)-2-(2,2-dimethyl-[1,3]dioxolan-4-yl)ethan-1-ol

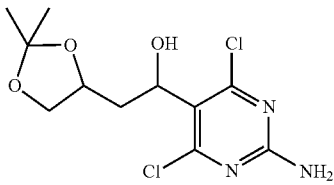

A mixture composed of 1-(2-amino-4,6-dichloropyrimidin-5-yl)-3-buten-1-ol (57.24 g), N-methylmorpholine-N-oxide (147.6 g), tetrahydrofuran (500 ml), acetone (500 ml), water (500 ml) and osmium tetroxide (62 mg) was stirred at room temperature for 2 days. After the disappearance of the materials had been confirmed, a saturated aqueous sodium thiosulfate solution (1 L) was added to the reaction solution, and the reaction mixture was then concentrated to approximately 1.5 L under reduced pressure. The residue was saturated with sodium chloride, followed by extraction with tetrahydrofuran. The organic layer was dried over anhydrous sodium sulfate. After filtration, the filtrate was concentrated under reduced pressure, and the solvent was then distilled away. N,N-Dimethylformamide (500 ml), 2,2-dimethoxypropane (210 ml) and p-toluenesulfonic acid monohydrate (18.61 g) were added to the resulting residue. The resulting mixture was stirred at room temperature for 14 hours. A saturated sodium bicarbonate solution (1 L) and water (1 L) were added to the reaction mixture, followed by extraction with ethyl acetate. The organic layer was successively washed with water and saturated saline in this order, and it was then dried over anhydrous sodium sulfate. After filtration, the filtrate was concentrated to about 100 ml under reduced pressure. Hexane was added to the residue, and the precipitate was then collected by filtration, so as to obtain the title compound (53.88 g) as a solid.

$^1$H-NMR (DMSO-D$_6$) δ: 1.22-1.32 (6H, m), 1.72-2.23 (2H, m), 2.50 (1H, s), 3.50 (1H, td, J=14.2, 6.9 Hz), 4.22-3.92 (2H, m), 5.06-5.36 (2H, m), 7.43 (2H, d, J=12.8 Hz).

ESI-MS m/z: 308 (M+H)$^+$.

(3) 1-(2-Amino-4,6-dichloropyrimidin-5-yl)-2-(2,2-dimethyl-[1,3]dioxolan-4-yl)ethan-1-one

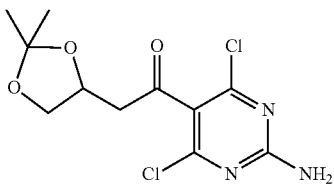

Acetic anhydride (149 ml) was added dropwise to a mixture composed of the above 1-(2-amino-4,6-dichloropyrimidin-5-yl)-2-(2,2-dimethyl-[1,3]dioxolan-4-yl)ethan-1-ol (74.70 g) and dimethyl sulfoxide (600 ml) at room temperature over 15 minutes under cooling in an ice bath. The reaction mixture was then stirred at the same temperature as above for 18 hours. After the disappearance of the materials had been confirmed, the reaction solution was poured into ice water. The precipitated solid was collected by filtration, so as to obtain the title compound (68.26 g).

$^1$H-NMR (CDCl$_3$) δ: 1.37 (3H, s), 1.42 (3H, s), 2.98-3.06 (1H, m), 3.32-3.40 (1H, m), 3.67-3.72 (1H, m), 4.25-4.30 (1H, m), 4.57-4.64 (1H, m), 5.72 (2H, s).

ESI-MS m/z: 306 (M+H)$^+$.

(4) 4-Chloro-3-[(2,2-dimethyl-1,3-dioxolan-4-yl)methyl]-1-(4-methoxybenzyl)-1H-pyrazolo[3,4-d]pyrimidine-6-amine

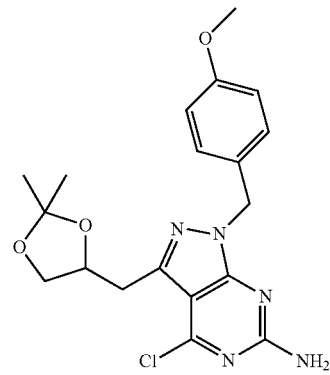

Triethylamine (83.68 ml) was added to a mixture composed of the above 1-(2-amino-4,6-dichloropyrimidin-5-yl)-2-(2,2-dimethyl-[1,3]dioxolan-4-yl)ethan-1-one (61.23 g), (4-methoxybenzyl)-hydrazine hydrochloride (41.50 g) produced by the method described in U.S. Patent No. US2003/18197, and dichloromethane (600 ml) over 30 minutes under cooling in an ice bath. Thereafter, while the temperature of the reaction solution was gradually raised, it was stirred for 17 hours. Thereafter, a 10% citric acid aqueous solution was added to the reaction mixture, followed by extraction with dichloromethane. The organic layer was dried over anhydrous sodium sulfate and was then concentrated under reduced pressure. A 5% citric acid aqueous solution was added to the resulting residue, and the precipitate was then collected by filtration. The resultant was washed with water, so as to obtain the title compound (73.84 g) as a solid.

$^1$H-NMR (CDCl$_3$) δ: 1.36 (3H, s), 1.43 (3H, s), 3.11 (1H, dd, J=14.7, 8.1 Hz), 3.43 (1H, dd, J=14.7, 5.2 Hz), 3.73-3.78 (4H, m), 4.08 (1H, dd, J=8.1, 6.0 Hz), 4.54-4.61 (1H, m), 4.77 (2H, brs), 5.22 (2H, s), 6.83 (2H, d, J=8.5 Hz), 7.24 (2H, d, J=8.5 Hz).

ESI-MS m/z: 404 (M+H)$^+$.

(5) Di-tert-butyl{4-chloro-3-[(2,2-dimethyl-1,3-dioxolan-4-yl)methyl]-1-(4-methoxybenzyl)-1H-pyrazolo[3,4-d]pyrimidin-6-yl}imide dicarbonate

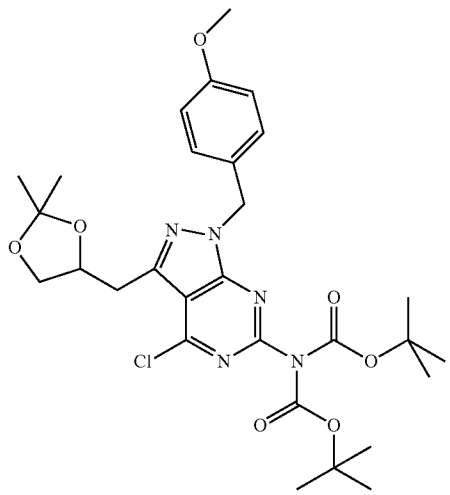

4-Dimethylaminopyridine (2.20 g) and di-tert-butyl dicarbonate (86.59 g) were added to a mixture composed of the above 4-chloro-3-[(2,2-dimethyl-1,3-dioxolan-4-yl)methyl]-1-(4-methoxybenzyl)-1H-pyrazolo[3,4-d]pyrimidine-6-amine (72.83 g) and tetrahydrofuran (700 ml), and the resulting mixture was then stirred at room temperature for 12 hours. Thereafter, the reaction mixture was filtered, and the filtrate was then concentrated under reduced pressure. The resulting residue was purified by silica gel column chromatography (ethyl acetate-hexane), so as to obtain the title compound (70.00 g) as an amorphous substance.

$^1$H-NMR (CDCl$_3$) δ: 1.37 (3H, s), 1.40 (3H, s), 1.44-1.46 (18H, m), 3.21-3.29 (1H, m), 3.48-3.55 (1H, m), 3.74-3.81 (4H, m), 4.09-4.15 (1H, m), 4.58-4.66 (1H, m), 5.48 (2H, dd, J=17.3, 15.1 Hz), 6.81 (2H, d, J=7.8 Hz), 7.27-7.30 (2H, m).

ESI-MS m/z: 604 (M+H)$^+$.

(6) Di-tert-butyl[4-chloro-3-(2,3-dihydroxypropyl)-1-(4-methoxybenzyl)-1H-pyrazolo[3,4-d]pyrimidin-6-yl]imide dicarbonate

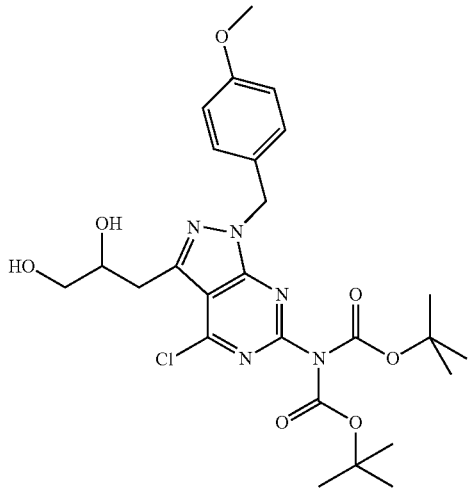

The above di-tert-butyl{4-chloro-3-[(2,2-dimethyl-1,3-dioxolan-4-yl)methyl]-1-(4-methoxybenzyl)-1H-pyrazolo[3,4-d]pyrimidin-6-yl}imide dicarbonate (53.85 g) was dissolved in acetonitrile (500 ml), and copper(II) chloride dihydrate (30.39 g) was then added to the solution. The resulting mixture was stirred at room temperature for 2 hours. Thereafter, a saturated ammonium chloride aqueous solution was added to the reaction solution, followed by extraction with ethyl acetate. The organic layer was washed with saturated saline, and it was then dried over anhydrous sodium sulfate, followed by concentration under reduced pressure. The resulting residue was purified by silica gel column chromatography (ethyl acetate-hexane), so as to obtain the title compound (37.70 g) as an amorphous substance.

$^1$H-NMR (CDCl$_3$) δ: 1.46 (18H, s), 3.15 (1H, d, J=3.7 Hz), 3.23-3.33 (2H, m), 3.62-3.82 (5H, m), 4.26-4.34 (1H, m), 5.49 (2H, t, J=15.9 Hz), 6.82 (2H, d, J=8.1 Hz), 7.25-7.30 (2H, m).

ESI-MS m/z: 564 (M+H)$^+$.

(7) Di-tert-butyl[8-hydroxy-2-(4-methoxybenzyl)-2,7,8,9-tetrahydro-6-thia-1,2,3,5-tetraazabenzo[cd]azulen-4-yl]imide dicarbonate

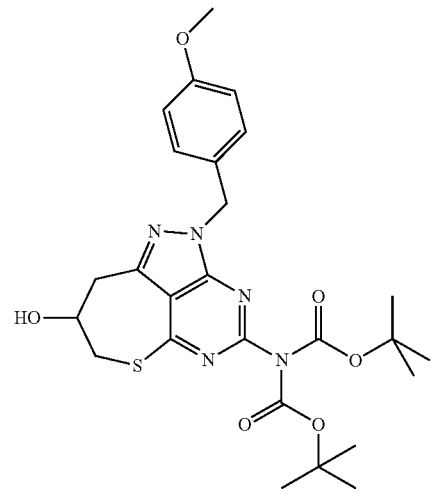

Methanesulfonyl chloride (4.23 ml) was added dropwise to a mixture composed of the above di-tert-butyl[4-chloro-3-(2,3-dihydroxypropyl)-1-(4-methoxybenzyl)-1H-pyrazolo[3,4-d]pyrimidin-6-yl]imide dicarbonate (28.00 g), 2,4,6-collidine (16.53 ml) and anhydrous dichloromethane (400 ml) under cooling in an ice bath. The resulting mixture was then stirred at 4° C. for 15 hours. Thereafter, a 10% citric acid aqueous solution was added to the reaction mixture, followed by extraction with dichloromethane. The organic layer was dried over anhydrous sodium sulfate, and it was then concentrated under reduced pressure. The resulting residue was dissolved in N,N-dimethylformamide (300 ml), and sodium hydrogensulfide monohydrate (5.52 g) was then added to the solution under cooling in an ice bath. Thereafter, the resulting mixture was stirred at room temperature for 1.5 hours. Thereafter, potassium carbonate (10.29 mg) was added to the reaction mixture, and the resulting mixture was then heated to 50° C., followed by a further stirring operation for 5 hours. Subsequently, ethyl acetate was added to the reaction mixture, and the resultant was then successively washed with a 10% citric acid aqueous solution and then with a saturated saline. The resultant was dried over anhydrous sodium sulfate, and it was then concentrated under reduced pressure. The resulting residue was purified by silica gel column chromatography (ethyl acetate-hexane), so as to obtain the title compound (20.59 g) as a solid.

$^1$H-NMR (CDCl$_3$) δ: 1.45 (18H, s), 2.39 (1H, brs), 3.29-3.51 (4H, m), 4.58 (1H, brs), 3.76 (3H, s), 5.42-5.49 (2H, m), 6.82 (2H, d, J=8.6 Hz), 7.30 (2H, d, J=8.6 Hz).

ESI-MS m/z: 544 (M+H)$^+$.

(8) 4-[Bis(tert-butoxycarbonyl)amino]-2-(4-methoxybenzyl)-2,7-dihydro-6-thia-1,2,3,5-tetraazabenzo[cd]azulen-8-yl acetate

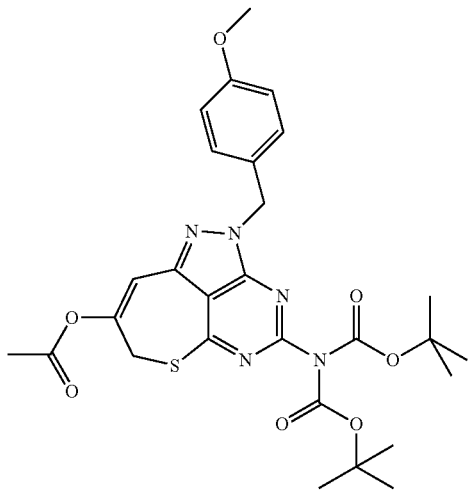

In a nitrogen atmosphere, acetic anhydride (14 ml) was added dropwise to a mixture composed of the above di-tert-butyl[8-hydroxy-2-(4-methoxybenzyl)-2,7,8,9-tetrahydro-6-thia-1,2,3,5-tetraazabenzo[cd]azulen-4-yl]imide dicarbonate (8.17 g), dimethyl sulfoxide (74 ml), and pyridine (12 ml) under cooling on ice, and the resulting mixture was then stirred for 30 minutes. Thereafter, the reaction solution was further stirred at room temperature for 15 hours. After the disappearance of the materials had been confirmed, the reaction mixture was diluted with ethyl acetate, and it was then washed with a saturated saline. The organic layer was dried over anhydrous sodium sulfate, followed by concentration under reduced pressure. The resulting residue was purified by silica gel column chromatography (ethyl acetate-hexane), so as to obtain the title compound (6.15 g) as an amorphous substance.

$^1$H-NMR (CDCl$_3$) δ: 1.44 (18H, s), 2.26 (3H, s), 3.77 (3H, s), 3.88 (2H, s), 5.50 (2H, s), 6.68 (1H, s), 6.83 (2H, d, J=8.8 Hz), 7.31 (2H, d, J=8.8 Hz).

ESI-MS m/z: 584 (M+H)$^+$.

(9) Di-tert-butyl[2-(4-methoxybenzyl)-8-oxo-2,7,8,9-tetrahydro-6-thia-1,2,3,5-tetraazabenzo[cd]azulen-4-yl]imide dicarbonate

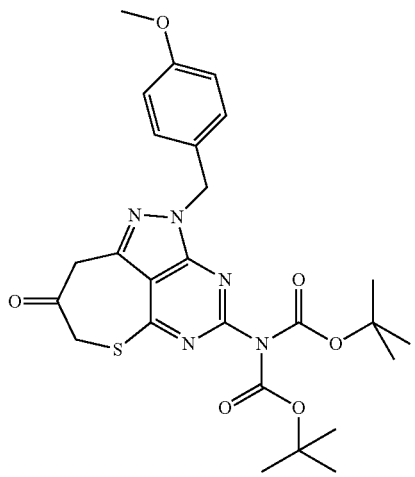

A mixture composed of the above 4-[bis(tert-butoxycarbonyl)amino]-2-(4-methoxybenzyl)-2,7-dihydro-6-thia-1,2,3,5-tetraazabenzo[cd]azulen-8-yl acetate (6.15 g), methanol (200 ml), and potassium carbonate (0.73 g) was stirred for 1.5 hours under cooling in an ice bath. After the disappearance of the materials had been confirmed, a saturated ammonium chloride aqueous solution was added to the reaction mixture, followed by extraction with ethyl acetate. The organic layer was washed with a saturated saline, and it was then dried over anhydrous sodium sulfate, followed by concentration under reduced pressure, so as to obtain the title compound (5.70 g) as an amorphous substance.

$^1$H-NMR (CDCl$_3$) δ: 1.46 (18H, s), 3.84 (2H, s), 3.77 (3H, s), 4.23 (2H, s), 5.48 (2H, s), 6.83 (2H, d, J=8.6 Hz), 7.32 (2H, d, J=8.6 Hz).

ESI-MS m/z: 542 (M+H)$^+$.

(10) Ethyl {4-[bis(tert-butoxycarbonyl)amino]-2-(4-methoxybenzyl)-2,7-dihydro-6-thia-1,2,3,5-tetraazabenzo[cd]azulen-8-yl}acetate

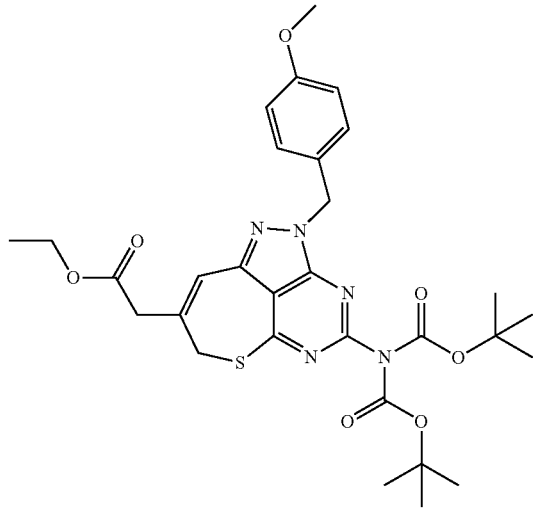

A mixture composed of the above di-tert-butyl[2-(4-methoxybenzyl)-8-oxo-2,7,8,9-tetrahydro-6-thia-1,2,3,5-tetraazabenzo[cd]azulen-4-yl]imide dicarbonate (5.19 g), ethyl (triphenylphosphanylidene)acetate (3.51 g), and toluene (300 ml) was stirred at 65° C. for 13 hours. Thereafter, the reaction mixture was concentrated under reduced pressure, and the residue was then purified by silica gel column chromatography (ethyl acetate-hexane), so as to obtain the title compound (3.78 g) as an amorphous substance.

$^1$H-NMR (CDCl$_3$) δ: 1.29 (3H, t, J=7.1 Hz), 1.69-1.77 (1H, m), 2.37-2.40 (1H, m), 2.46-2.52 (1H, m), 2.68-2.71 (2H, m), 4.20 (2H, q, J=7.1 Hz), 5.10-5.13 (1H, m), 5.20 (2H, brs).

ESI-MS m/z: 612 (M+H)$^+$

(11) 2-(4-amino-2,7-dihydro-6-thia-1,2,3,5-tetraazabenzo[cd]azulen-8-yl)-N-methylacetamide trifluoroacetate

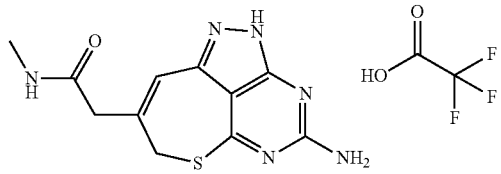

The above ethyl {4-[bis(tert-butoxycarbonyl)amino]-2-(4-methoxybenzyl)-2,7-dihydro-6-thia-1,2,3,5-tetraazabenzo[cd]azulen-8-yl}acetate (2.2 g) was dissolved in a 40% methylamine/methanol solution (40 ml), and the mixed solution was then stirred at room temperature for 2 hours. The completion of the reaction was confirmed by LC-MS, and the solvent was then distilled away under reduced pressure. Thereafter, anisole (2 ml) and trifluoroacetic acid (40 ml) were added to the resulting residue, and the resulting mixture was then stirred at 65° C. for 15 hours. Thereafter, the reaction solution was concentrated under reduced pressure, and an isopropyl ether-ether mixed solution was then added to the residue. The precipitate was collected by filtration, so as to obtain the title compound (1.53 g) as a solid.

ESI-MS m/z: 277 (M+H)+.

(12) 5-Chloro-4-hydroxy-6-methylnicotinic acid

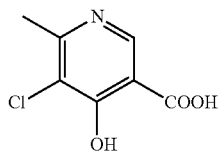

Commercially available 4-hydroxy-6-methyl-nicotinic acid (300 mg) was suspended in 3 ml of acetonitrile, and N-chlorosuccinimide (380 mg) was then added to the suspension. The resulting mixture was stirred at room temperature for 30 minutes. Thereafter, the reaction solution was heated under reflux for 45 minutes. After the disappearance of the materials had been confirmed, the reaction solution was cooled on ice, and the precipitate was then collected by filtration, so as to obtain the title compound (324 mg) as a solid.

$^1$H-NMR (CD$_3$OD) δ: 2.56 (3H, s), 8.50 (1H, s).
ESI-MS m/z: 188 (M+H)+

(13) Methyl 4,5-dichloro-6-methylnicotinate

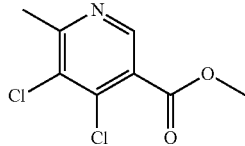

Phosphorus oxychloride (1.13 ml) was added to the above 5-chloro-4-hydroxy-6-methylnicotinic acid (320 mg), and the resulting mixture was then heated under reflux for 2 hours. Thereafter, the reaction solution was concentrated under reduced pressure, and methanol (3 ml) was then added dropwise to the residue under cooling on ice. The resulting mixture was stirred at room temperature for 30 minutes, followed by concentration under reduced pressure. A saturated sodium bicarbonate solution was added to the residue under cooling on ice, followed by extraction with ethyl acetate. The organic layer was dried over anhydrous sodium sulfate, and the solvent was then distilled away, so as to obtain a crude product of the title compound (436 mg) as a solid.

ESI-MS m/z: 220 (M+H)+

(14) Methyl 5-chloro-4-methoxy-6-methylnicotinate

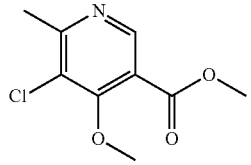

Crude methyl 4,5-dichloro-6-methylnicotinate (380 mg) was dissolved in 3 ml of methanol and, in a nitrogen stream, sodium methoxide (120 mg) was then added to the solution under cooling on ice. The temperature of the reaction solution was gradually raised to room temperature, and it was stirred for 18 hours. After the disappearance of the materials had been confirmed, a saturated ammonium chloride aqueous solution was added to the reaction solution under cooling on ice, followed by extraction with chloroform. The organic layer was dried over anhydrous sodium sulfate, and the solvent was then distilled away. The residue was purified by silica gel chromatography (ethyl acetate-hexane), so as to obtain the title compound (210 mg) as a solid.

$^1$H-NMR (CDCl$_3$) δ: 2.67 (3H, s), 3.95 (4H, s), 4.00 (3H, s), 8.76 (1H, s).
ESI-MS m/z: 216 (M+H)+

(15) (5-Chloro-4-methoxy-6-methylpyridin-3-yl)methanol

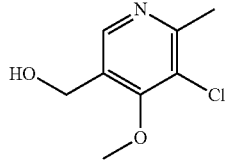

The above methyl 5-chloro-4-methoxy-6-methylnicotinate (1.0 g) was dissolved in 30 ml of methanol, and sodium borohydride (1.75 g) was then added to the solution. The resulting mixture was heated under reflux for 1 hour. Thereafter, a saturated ammonium chloride aqueous solution was added to the reaction solution under cooling on ice, followed by extraction with chloroform three times. The organic layer was dried over anhydrous sodium sulfate, and the solvent was then distilled away, so as to obtain the title compound (0.92 g) as an oily substance.

$^1$H-NMR (CDCl$_3$) δ: 2.63 (3H, s), 4.00 (3H, s), 4.71 (2H, brs), 8.33 (1H, s)
ESI-MS m/z: 188 (M+H)+

(16) 3-Chloro-5-(chloromethyl)-4-methoxy-2-methylpyridine

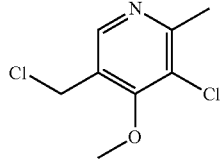

The above (5-chloro-4-methoxy-6-methylpyridin-3-yl)methanol (520 mg) was dissolved in 20 ml of chloroform, and thionyl chloride (0.38 ml) was then added to the solution under cooling on ice. The resulting mixture was stirred at the same temperature as above for 3 hours. Thereafter, the reaction solution was concentrated, and ethyl acetate was then added to the concentrate. The resulting mixture was washed with saturated sodium bicarbonate solution, water, and saturated saline in this order. The organic layer was dried over anhydrous sodium sulfate, and the solvent was then distilled away. The residue was purified by silica gel chromatography (ethyl acetate-hexane), so as to obtain the title compound (550 mg) as an oily substance.

$^1$H-NMR (CDCl$_3$) δ: 2.64 (3H, s), 4.05 (3H, s), 4.61 (2H, s), 8.35 (1H, s).

ESI-MS m/z: 206 (M+H)+

(17) 3-Chloro-4-methoxy-2,5-dimethylpyridine

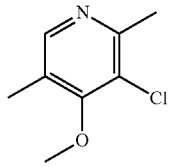

The above 3-chloro-5-(chloromethyl)-4-methoxy-2-methylpyridine (550 mg) was dissolved in 10 ml of methanol, and 10% Pd carbon (50 mg) was then added to the solution. Normal-pressure contact hydrogenation was performed on the mixture under cooling on ice for 3 hours. Thereafter, the catalyst was removed by filtration, and methanol was then distilled away under reduced pressure. The residue was extracted with chloroform. The organic layer was washed with a saturated sodium bicarbonate solution, and it was then dried over anhydrous sodium sulfate. The solvent was distilled away, and the residue was purified by silica gel chromatography (ethyl acetate-hexane), so as to obtain the title compound (365 mg) as an oily substance.

$^1$H-NMR (CDCl$_3$) δ: 2.25 (3H, s), 2.59 (3H, s), 3.89 (3H, s), 8.16 (1H, s).

ESI-MS m/z: 172 (M+H)+

(18) 3-Chloro-4-methoxy-2,5-dimethylpyridine 1-oxide

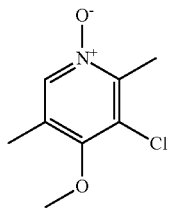

The above 3-chloro-4-methoxy-2,5-dimethylpyridine (181 mg) was dissolved in 5 ml of dichloromethane, and urea peroxide (169 mg) and phthalic anhydride (219 mg) were then added to the solution. The resulting mixture was stirred at room temperature for 2.5 hours. Thereafter, a saturated aqueous sodium thiosulfate solution was added to the reaction solution under cooling on ice, and the resulting mixture was then diluted with chloroform. The water layer was extracted with chloroform two times. The organic layer was dried over anhydrous sodium sulfate, and the solvent was then distilled away, so as to obtain the title compound (181 mg) as a solid.

$^1$H-NMR (CDCl$_3$) δ: 2.24 (3H, s), 2.62 (3H, s), 3.87 (3H, s), 8.07 (1H, s).

ESI-MS m/z: 188 (M+H)+

(19) (3-Chloro-4-methoxy-5-methylpyridin-2-yl)methanol

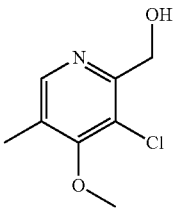

The above 3-chloro-4-methoxy-2,5-dimethylpyridine 1-oxide (530 mg) was suspended in 15 ml of dichloromethane, and trifluoroacetic anhydride (0.39 ml) was then added to the suspension under cooling on ice. The resulting mixture was stirred at room temperature for 3 hours. The reaction solution was diluted with chloroform, and was then washed with a saturated sodium bicarbonate solution. The water layer was extracted with chloroform. The organic layer was dried over anhydrous sodium sulfate, and the solvent was then distilled away, so as to obtain the title compound (521 mg) as an oily substance.

$^1$H-NMR (CDCl$_3$) δ: 2.29 (3H, s), 3.93 (3H, s), 4.29 (1H, brs), 4.72-4.74 (2H, m), 8.26 (1H, s).

ESI-MS m/z: 188 (M+H)+

(20) 3-Chloro-2-(chloromethyl)-4-methoxy-5-methylpyridine hydrochloride

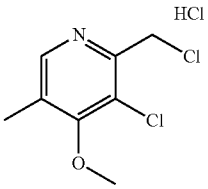

The above (3-chloro-4-methoxy-5-methylpyridin-2-yl)methanol (530 mg) was dissolved in 20 ml of chloroform, and thionyl chloride (1.03 ml) was then added dropwise to the solution under cooling on ice. The resulting mixture was stirred at room temperature for 3 hours. Thereafter, the reaction solution was concentrated, and it was then washed with a mixed solvent of ether-hexane, so as to obtain the title compound (410 mg) as a solid.

$^1$H-NMR (CDCl$_3$) δ: 2.47 (3H, s), 4.32 (3H, s), 5.09 (2H, s), 8.54 (1H, s).

ESI-MS m/z: 206 (M+H)+

(21) 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide

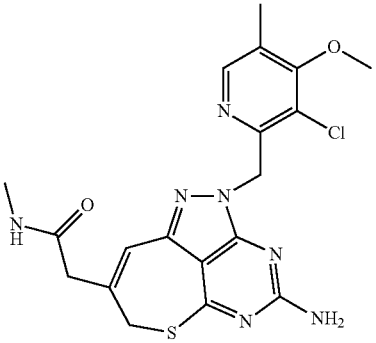

Dimethylformamide (1 ml) was added to 2-(4-amino-2,7-dihydro-6-thia-1,2,3,5-tetraazabenzo[cd]azulen-8-yl)-N-methylacetamide trifluoroacetate (28 mg), 3-chloro-2-(chloromethyl)-4-methoxy-5-methylpyridine hydrochloride (36 mg), and potassium carbonate (69 mg). The resulting mixture was stirred at 60° C. for 2.5 hours. Thereafter, the insoluble matter was removed by filtration, and the solvent was then distilled away in a nitrogen stream. The resulting residue was dissolved in dimethyl sulfoxide (1 ml), and it was then purified by preparatory reverse-phase HPLC. The solvent was distilled away under reduced pressure, so as to obtain the title compound (27.0 mg) as a solid.

$^1$H-NMR (CDCl$_3$) δ: 2.24 (4H, s), 2.82 (3H, d, J=4.9 Hz), 3.27 (2H, s), 3.80 (2H, s), 3.91 (3H, s), 5.21 (2H, s), 5.65 (2H, s), 5.87 (1H, s), 6.70 (1H, s), 8.16 (1H, s).

ESI-MS m/z: 446 (M+H)$^+$.

Example 2

(1) 5-Bromo-2,3-dimethyl-4-nitropyridine 1-oxide

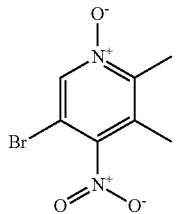

5-Bromo-2,3-dimethylpyridine 1-oxide (4.61 g) produced by the method described in U.S. Pat. No. 5,250,527 was dissolved in concentrated sulfuric acid (10 ml). Thereafter, a mixed solution of fuming nitric acid (24 ml) and fuming sulfuric acid (13 ml) was added dropwise to the solution obtained above under stirring and cooling on ice. The resulting mixture was stirred at the same temperature as above for 30 minutes, and was then stirred at 90° C. for 1 hour. After leaving to cool, the reaction solution was poured into ice water. Dichloromethane was added to the reaction solution under stirring and cooling in an ice bath, and the mixture was then neutralized with ammonia water. The reaction solution was extracted with dichloromethane. The organic layer was dried over anhydrous magnesium sulfate, and the solvent was then distilled away under reduce pressure, so as to obtain a crude product of the title compound (4.80 g) as a solid.

(2) 5-Bromo-4-methoxy-2,3-dimethylpyridine 1-oxide

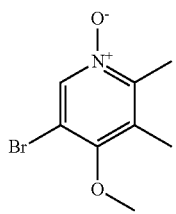

A 1 M sodium methoxide-methanol solution (30 ml) was added to a methanol (20 ml) solution of the above 5-bromo-2,3-dimethyl-4-nitropyridine 1-oxide (4.80 g) under cooling in an ice bath, and the resulting mixture was stirred at room temperature overnight. Thereafter, the reaction solution was concentrated, and the residue was dissolved in dichloromethane and water for liquid separation. The organic layer was dried over anhydrous sodium sulfate, and the filtrate was then concentrated, so as to obtain a crude product of the title compound (4.91 g) as a solid.

$^1$H-NMR (CDCl$_3$) δ: 2.30 (3H, s), 2.47 (3H, s), 3.84 (3H, s), 8.36 (1H, s).

ESI-MS m/z: 232 (M+H)$^+$ (3) (5-Bromo-4-methoxy-3-methylpyridin-2-yl)methanol

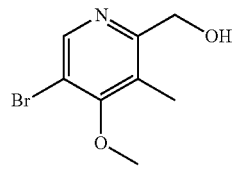

5-Bromo-4-methoxy-2,3-dimethylpyridine 1-oxide (4.91 g) was dissolved in dichloromethane (60 ml), and trifluoroacetic anhydride (20 ml) was then added to the solution at room temperature. The resulting mixture was stirred overnight. Thereafter, the reaction solution was concentrated, and the concentrated solution was then dissolved in methanol (50 ml). The resulting mixture was stirred at 50° C. for 1 hour. The reaction solution was concentrated. The residue was dissolved in dichloromethane, and was then washed with a saturated sodium bicarbonate solution. The organic layer was dried over anhydrous sodium sulfate, and the filtrate was then concentrated. The residue was purified by silica gel column chromatography (hexane-ethyl acetate), so as to obtain the title compound (3.43 g) as a solid.

$^1$H-NMR (CDCl$_3$) δ: 2.17 (3H, s), 3.89 (3H, s), 4.62 (2H, s), 8.50 (1H, s).

ESI-MS m/z: 232 (M+H)$^+$ (4) 5-Bromo-2-({[tert-butyl(dimethyl)silyl]oxy}methyl)-4-methoxy-3-methylpyridine

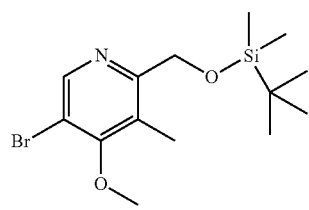

The above (5-bromo-4-methoxy-3-methylpyridin-2-yl)methanol (500 mg) was dissolved in dichloromethane (10 ml), and t-butyldimethylsilyl chloride (487 mg), triethylamine (0.48 ml), and dimethylaminopyridine (30 mg) were then added to the solution under cooling in an ice bath. The resulting mixture was stirred at room temperature overnight. Thereafter, the reaction solution was diluted with dichloromethane, and was then washed with a saturated sodium bicarbonate solution. The organic layer was dried over anhydrous sodium sulfate, and the filtrate was then concentrated. The residue was purified by silica gel column chromatography (hexane-ethyl acetate), so as to obtain the title compound (743 mg) as an oily substance.

$^1$H-NMR (CDCl$_3$) δ: 0.07 (6H, s), 0.89 (9H, s), 2.37 (3H, s), 3.87 (3H, s), 4.77 (2H, s), 8.43 (1H, s).

(5) 2-({[tert-butyl(dimethyl)silyl]oxy}methyl)-5-fluoro-4-methoxy-3-methylpyridine

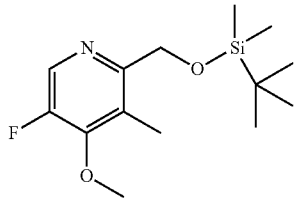

The above 5-bromo-2-({[tert-butyl(dimethyl)silyl]oxy}methyl)-4-methoxy-3-methylpyridine (734 mg) was dissolved in tetrahydrofuran (30 ml), and butyllithium (1.59 M solution, 2.42 ml) was then added dropwise to the solution at −110° C. The resulting mixture was stirred at the same above temperature for 1 hour, and a tetrahydrofuran (5 ml) solution of N-fluorobenzenesulfonimide (3.03 g) was then added dropwise to the reaction solution at the same temperature. The temperature of the resulting mixture was gradually raised to −68° C. over 3 hours, and the mixture was then stirred at room temperature for 30 minutes. Thereafter, a saturated ammonium chloride aqueous solution was added to the reaction solution, followed by extraction with dichloromethane. The organic layer was dried over anhydrous sodium sulfate, and the filtrate was then concentrated. The residue was purified by silica gel column chromatography (hexane-ethyl acetate), so as to obtain the title compound (353 mg) as an oily substance.

$^1$H-NMR (CDCl$_3$) δ: 0.06 (6H, s), 0.89 (9H, s), 2.28 (3H, s), 4.07 (3H, d, J=3.7 Hz), 4.75 (2H, s), 8.15 (1H, d, J=3.7 Hz).

ESI-MS m/z: 286 (M+H)$^+$.

(6) (5-Fluoro-4-methoxy-3-methylpyridin-2-yl)methanol

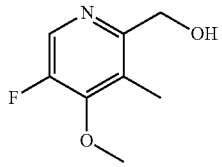

Tetrabutylammonium fluoride (1 M solution, 1.49 ml) was added to a tetrahydrofuran (10 ml) solution of the above 2-({[tert-butyl(dimethyl)silyl]oxy}methyl)-5-fluoro-4-methoxy-3-methylpyridine (353 mg) under cooling in an ice bath, and the resulting mixture was stirred at room temperature for 1 hour. The reaction solution was diluted with dichloromethane, and was then washed with water. The organic layer was dried over anhydrous sodium sulfate, and the filtrate was then concentrated. The residue was purified by silica gel column chromatography (hexane-ethyl acetate), so as to obtain the title compound (150 mg) as a solid.

$^1$H-NMR (CDCl$_3$) δ: 2.08 (3H, s), 4.10 (3H, d, J=4.1 Hz), 4.52 (1H, s), 4.61 (2H, s), 8.22 (1H, d, J=4.1 Hz).

ESI-MS m/z: 172 (M+H)$^+$.

(7) 2-(Chloromethyl)-5-fluoro-4-methoxy-3-methylpyridine hydrochloride

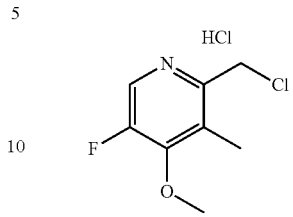

The title compound (154 mg) was obtained as a solid by the same synthesis method as in Example 1(20) using the above (5-fluoro-4-methoxy-3-methylpyridin-2-yl)methanol (135 mg).

ESI-MS m/z: 190 (M+H)$^+$.

(8) 2-{4-Amino-2-[(5-fluoro-4-methoxy-3-methylpyridin-2-yl)methyl]-2,7-dihydro-6-thia-1,2,3,5-tetraazabenzo-[cd]azulen-8-yl}-N-methylacetamide

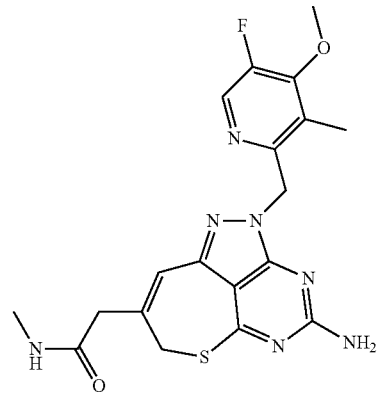

Potassium carbonate (85 mg) and 2-(chloromethyl)-5-fluoro-4-methoxy-3-methylpyridine hydrochloride (52 mg) were added to an N,N-dimethylformamide (5 ml) solution of 2-(4-amino-2,7-dihydro-6-thia-1,2,3,5-tetraazabenzo[cd]azulen-8-yl)-N-methylacetamide trifluoroacetate (60 mg). The resulting mixture was stirred at 50° C. for 3.5 hours. Thereafter, insoluble matter was removed by filtration, and the filtrate was then concentrated. The residue was purified by silica gel column chromatography (chloroform-methanol), so as to obtain the title compound (30 mg) as a solid.

$^1$H-NMR (CDCl$_3$) δ: 2.27 (3H, s), 2.83 (3H, d, J=4.6 Hz), 3.27 (2H, s), 3.78 (2H, s), 4.08 (3H, d, J=4.6 Hz), 5.13 (2H, s), 5.49 (2H, s), 5.74 (1H, brs), 6.70 (1H, s), 8.19 (1H, d, J=3.4 Hz).

ESI-MS m/z: 430 (M+H)$^+$.

Anal. Calcd. For C$_{19}$H$_{20}$FN$_7$O$_2$S.0.5H$_2$O: C, 52.05; H, 4.82; N, 22.36; F, 4.33; S, 7.32.

Found: C, 52.27; H, 4.79; N, 22.10; F, 4.44; S, 7.05.

Example 3

(1) 3-Bromo-2,5-dimethyl-4-nitropyridine 1-oxide

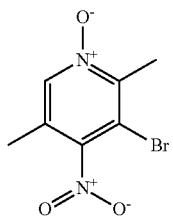

The title compound (1.08 g) was obtained as a solid by the same synthesis method as in Example 2(1) using commercially available 3-bromo-2,5-dimethylpyridine 1-oxide (2.35 g).

ESI-MS m/z: 247 (M+H)$^+$.

(2) 3-Bromo-4-methoxy-2,5-dimethylpyridine 1-oxide

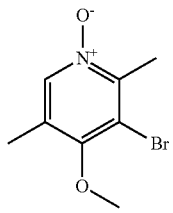

A crude product of the title compound (990 mg) was obtained as a solid by the same synthesis method as in Example 2(2) using the above 3-bromo-2,5-dimethyl-4-nitropyridine 1-oxide (1.08 g).

ESI-MS m/z: 234 (M+H)$^+$.

(3) (3-Bromo-4-methoxy-5-methylpyridin-2-yl)methanol

The title compound (931 mg) was obtained as a solid by the same synthesis method as in Example 2(3) using the above 3-bromo-4-methoxy-2,5-dimethylpyridine 1-oxide (990 mg).

$^1$H-NMR (CDCl$_3$) δ: 2.33 (3H, s), 3.90 (3H, s), 4.38 (1H, brs), 4.69 (2H, s), 8.28 (1H, s).

ESI-MS m/z: 234 (M+H)$^+$.

(4) 3-Bromo-2-(chloromethyl)-4-methoxy-5-pyridine hydrochloride

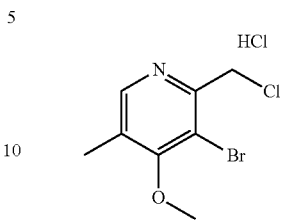

The title compound (161 mg) was obtained as a solid by the same synthesis method as in Example 1(20) using the above (3-bromo-4-methoxy-5-methylpyridin-2-yl)methanol (150 mg).

$^1$H-NMR (CDCl$_3$) δ: 2.50 (3H, s), 4.21 (3H, s), 5.18 (2H, s), 8.47 (1H, s).

ESI-MS m/z: 250 and 252 (M+H)$^+$.

(5) 2-{4-Amino-2-[(3-bromo-4-methoxy-5-methylpyridin-2-yl)methyl]-2,7-dihydro-6-thia-1,2,3,5-tetraazabenzo[cd]azulen-8-yl}-N-methylacetamide

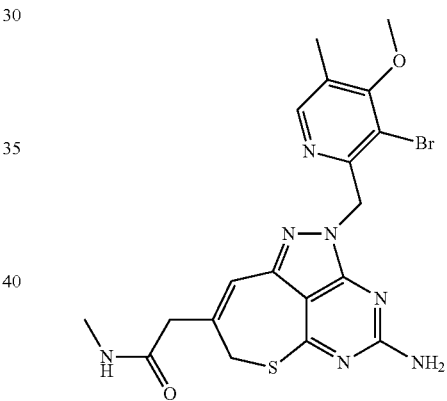

Potassium carbonate (160 mg) and 3-bormo-2-(chloromethyl)-4-methoxy-5-pyridine hydrochloride (166 mg) were added to an N,N-dimethylformamide (5 ml) solution of 2-(4-amino-2,7-dihydro-6-thia-1,2,3,5-tetraazabenzo[cd]azulen-8-yl)-N-methylacetamide trifluoroacetate (150 mg). The resulting mixture was stirred at 50° C. overnight. Thereafter, the reaction solution was diluted with dichloromethane, and was then washed with water. The organic layer was dried over anhydrous sodium sulfate, and the filtrate was then concentrated. The residue was purified by silica gel column chromatography (chloroform-methanol), so as to obtain the title compound (105 mg) as a solid.

$^1$H-NMR (CDCl$_3$) δ: 2.27 (3H, s), 2.83 (3H, d, J=4.6 Hz), 3.28 (2H, s), 3.81 (2H, s), 3.88 (3H, s), 5.08-5.14 (2H, brm), 5.66 (2H, s), 5.77 (1H, brs), 6.72 (1H, s), 8.17 (1H, s).

ESI-MS m/z: 492 (M+H)$^+$.

Anal. Calcd. For C$_{19}$H$_{20}$BrN$_7$O$_2$S0.25H$_2$O.0.2 dioxane: C, 46.40; H, 4.34; N, 19.13; Br, 15.59; S, 6.45.

Found: C, 46.21; H, 4.07; N, 19.16; Br, 15.70; S, 6.27.

Example 4

(1) Tert-butyl[8-(2-amino-2-oxoethyl)-2-(4-methoxybenzyl)-2,7-dihydro-6-thia-1,2,3,5-tetraazabenzo[cd]azulen-4-yl]carbamate

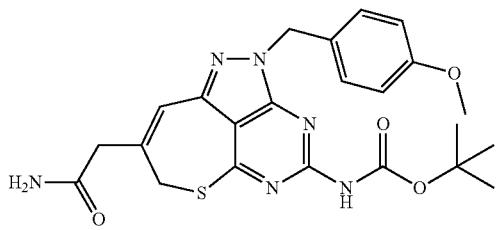

A 1 N sodium hydroxide aqueous solution (3 ml) was added to an ethanol (5 ml) solution of ethyl {4-[bis(tert-butoxycarbonyl)amino]-2-(4-methoxybenzyl)-2,7-dihydro-6-thia-1,2,3,5-tetraazabenzo[cd]azulen-8-yl}acetate (600 mg). The resulting mixture was stirred at room temperature overnight. Thereafter, 1 N hydrochloric acid (3 ml) was added to the reaction solution, and the resulting solution was then concentrated. Dichloromethane was added to the residue for extraction. The organic layer was dried over anhydrous sodium sulfate, and the filtrate was then concentrated to obtain carboxylic acid (576 mg). The carboxylic acid (576 mg) was dissolved in acetonitrile (10 ml), and ammonium chloride (157 mg), triethylamine (0.2 ml), and 1-ethyl-3-(3-dimethylaminopropyl)carbodiimide hydrochloride (282 mg) were then added to the solution. The resulting mixture was stirred at room temperature for 3 days. Thereafter, the reaction solution was diluted with dichloromethane, and water was then added thereto to carry out a liquid separation operation. The organic layer was washed with saturated saline. The organic layer was dried over anhydrous sodium sulfate, and the solvent was then distilled away under reduced pressure. The residue was purified by silica gel column chromatography (chloroform-methanol), so as to obtain the title compound (252 mg) as a solid.

ESI-MS m/z: 483 (M+H)$^+$

(2) 2-(4-Amino-2,7-dihydro-6-thia-1,2,3,5-tetraazabenzo[cd]azulen-8-yl)acetamide trifluoroacetate

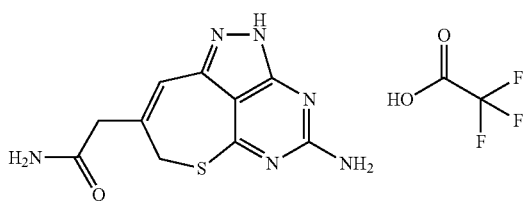

The title compound (162 mg) was obtained as a solid by the same synthesis method as in Example 1(11) using the above tert-butyl[8-(2-amino-2-oxoethyl)-2-(4-methoxybenzyl)-2,7-dihydro-6-thia-1,2,3,5-tetraazabenzo[cd]azulen-4-yl]carbamate (256 mg).

ESI-MS m/z: 263 (M+H)$^+$.

(3) 2-{4-Amino-2-[(3-bromo-4-methoxy-5-methylpyridin-2-yl)methyl]-2,7-dihydro-6-thia-1,2,3,5-tetraazabenzo[cd]azulen-8-yl}acetamide mesilate

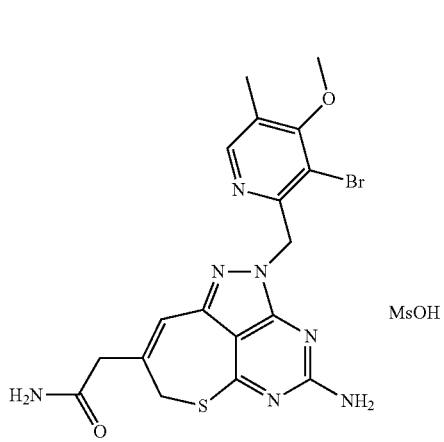

Potassium carbonate (110 mg) and 3-bromo-2-(chloromethyl)-4-methoxy-5-pyridine hydrochloride (114 mg) were added to an N,N-dimethylformamide (5 ml) solution of the above 2-(4-amino-2,7-dihydro-6-thia-1,2,3,5-tetraazabenzo[cd]azulen-8-yl)acetamide trifluoroacetate (100 mg). The resulting mixture was stirred at 50° C. overnight. Thereafter, the reaction solution was diluted with dichloromethane, and was then washed with water. The organic layer was dried over anhydrous sodium sulfate, and the filtrate was then concentrated. The residue was purified by silica gel column chromatography (chloroform-methanol), so as to obtain 2-{4-amino-2-[(3-bromo-4-methoxy-5-methylpyridin-2-yl)methyl]-2,7-dihydro-6-thia-1,2,3,5-tetraazabenzo[cd]azulen-8-yl}acetamide (90 mg) as a solid. The resulting solid (27 mg) was dissolved in dioxane, and a 0.2 M mesylate aqueous solution (0.283 ml) was then added to the solution under cooling in an ice bath, followed by freeze-drying, so as to obtain the title compound (32 mg) as a solid.

$^1$H-NMR (CDCl$_3$) δ: 2.30 (3H, s), 2.84 (3H, s), 3.35 (2H, d, J=0.9 Hz), 3.92 (3H, s), 3.95 (2H, s), 5.46 (1H, brs), 5.68 (2H, s), 5.97 (1H, brs), 6.75 (1H, s), 8.19 (1H, s).

ESI-MS m/z: 476 and 478 (M+H)$^+$.

Example 5

(1) 2-[4-Amino-2-(4-methoxybenzyl)-2,7-dihydro-6-thia-1,2,3,5-tetraazabenzo[cd]azulen-8-yl]-N-(2-fluoroethyl)acetamide

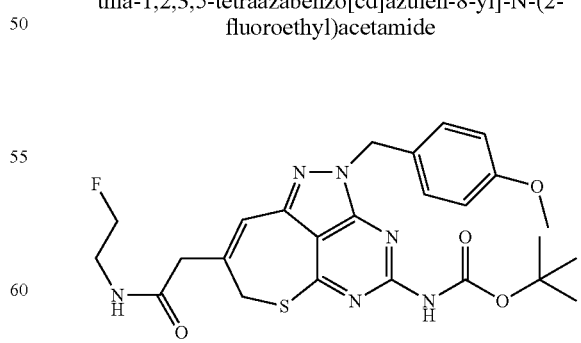

A 1 N sodium hydroxide aqueous solution (2.7 mL) was added to an ethanol (10 mL) solution of ethyl {4-[bis(tert-butoxycarbonyl)amino]-2-(4-methoxybenzyl)-2,7-dihydro-6-thia-1,2,3,5-tetraazabenzo[cd]azulen-8-yl}acetate (526 mg), and the resulting mixture was then stirred at room temperature overnight. Thereafter, the solvent was distilled away to obtain the sodium salt of carboxylic acid. This product was dissolved in N,N-dimethylformamide (10 mL), and 2-fluoroethylamine (171 mg), 1-ethyl-3-(3-dimethylaminopropyl) carbodiimide hydrochloride (247 mg), and 1-hydroxybenzotriazole (10 mg) were then added to the solution under cooling in an ice bath. The resulting mixture was stirred at room temperature for 3 days. Thereafter, the reaction solution was diluted with dichloromethane, and water was then added thereto to carry out a liquid separation operation. The organic layer was washed with a saturated saline. The organic layer was dried over anhydrous sodium sulfate, and the solvent was then distilled away under reduced pressure. The residue was purified by silica gel column chromatography (hexane-ethyl acetate), so as to obtain the title compound (419 mg) as an oily substance.

ESI-MS m/z: 529 (M+H)$^+$.

(2) 2-(4-Amino-2,7-dihydro-6-thia-1,2,3,5-tetraazabenzo[cd]azulen-8-yl)-N-(2-fluoroethyl)acetamide trifluoroacetate

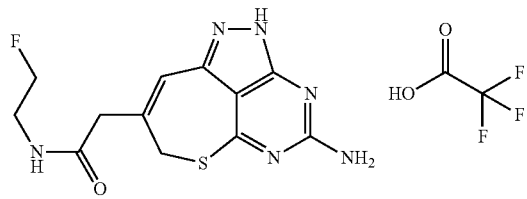

A crude product of the title compound (247 mg) was obtained as a solid by the same synthesis method as in Example 1(11) using the above 2-[4-amino-2-(4-methoxybenzyl)-2,7-dihydro-6-thia-1,2,3,5-tetraazabenzo[cd]azulen-8-yl]-N-(2-fluoroethyl)acetamide (418 mg).

ESI-MS m/z: 309 (M+H)$^+$.

(3) 2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-(2-fluoroethyl) acetamide

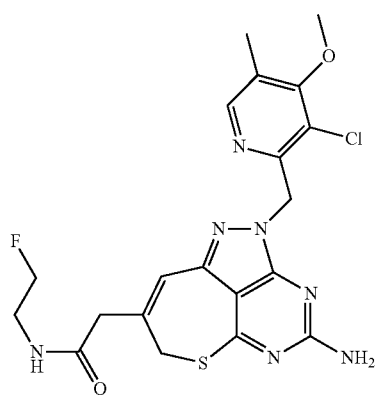

The title compound (12 mg) was obtained as a solid by the same synthesis method as in Example 3(5) using the above 2-(4-amino-2,7-dihydro-6-thia-1,2,3,5-tetraazabenzo[cd]azulen-8-yl)-N-(2-fluoroethyl)acetamide trifluoroacetate (60 mg) and 3-chloro-2-(chloromethyl)-4-methoxy-5-pyridine hydrochloride (52 mg).

$^1$H-NMR (CDCl$_3$) δ: 2.25 (3H, s), 3.31 (2H, s), 3.56 (1H, dd, J=10.5, 5.0 Hz), 3.63 (1H, dd, J=10.5, 5.0 Hz), 3.81 (2H, s), 3.91 (3H, s), 4.44 (1H, t, J=4.8 Hz), 4.56 (1H, t, J=4.8 Hz), 5.11 (2H, s), 5.65 (2H, s), 6.09 (1H, brs), 6.73 (1H, s), 8.17 (1H, s).

ESI-MS m/z: 478 (M+H)$^+$.

Anal. Calcd. For C$_{20}$H$_{21}$ClFN$_7$O$_2$S.0.75 dioxane: C, 50.80; H, 5.00; N, 18.02.

Found: C, 51.18; H, 4.86; N, 17.91.

Example 6

(1) 3-Chloro-4-methoxy-2-methylpyridine 1-oxide

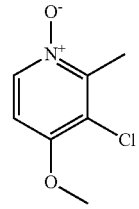

3-Chloro-2-methyl-4-nitropyridin-1-oxide (1.00 g) produced by the method described in Polish Journal of Chemistry, 1986, 59, 10-12 was dissolved in a 0.5 M sodium methoxide-methanol solution (15.9 mL), and the resulting mixture was then stirred at room temperature overnight. Thereafter, a saturated ammonium chloride aqueous solution was added to the reaction solution, and methanol was then distilled away under reduced pressure. The resultant was extracted with chloroform three times. The organic layer was dried over anhydrous magnesium sulfate, and the solvent was then distilled away under reduced pressure, so as to obtain the title compound (897 mg) as a solid.

$^1$H-NMR (CDCl$_3$) δ: 2.68 (3H, s), 3.96 (3H, s), 6.73 (1H, d, J=7.3 Hz), 8.20 (1H, d, J=7.3 Hz).

ESI-MS m/z: 174 (M+H)$^+$.

(2) (3-Chloro-4-methoxypyridin-2-yl)methyl acetate

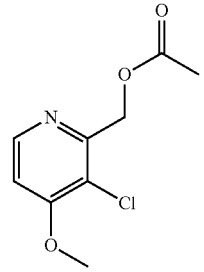

The above 3-chloro-4-methoxy-2-methylpyridin-1-oxide (890 mg) was dissolved in acetic anhydride (12 mL), and the resulting solution was then heated under reflux for 30 minutes. After leaving to cool to room temperature, the reaction solution was concentrated under reduced pressure, and the residue was then purified by silica gel chromatography (hexane-ethyl acetate), so as to obtain the title compound (576 mg) as an oily substance.

$^1$H-NMR (CDCl$_3$) δ: 2.17 (3H, s), 3.97 (3H, s), 5.33 (2H, s), 6.83 (1H, d, J=5.6 Hz), 8.39 (1H, d, J=5.6 Hz).

ESI-MS m/z: 216 (M+H)$^+$.

(3) (3-Chloro-4-methoxypyridin-2-yl)methanol

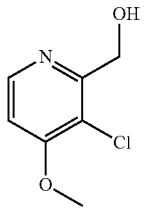

The above (3-chloro-4-methoxypyridin-2-yl)methyl acetate (570 mg) was dissolved in methanol (13 mL), and potassium carbonate (731 mg) was then added to the solution. The resulting mixture was stirred at 50° C. for 30 minutes. Thereafter, methanol was distilled away under reduced pressure, and water was then added to the residue, followed by extraction with chloroform three times. The organic layer was dried over anhydrous magnesium sulfate, and the solvent was then distilled away under reduced pressure, so as to obtain the title compound (437 mg) as an oily substance.

$^1$H-NMR (CDCl$_3$) δ: 3.98 (3H, s), 4.39 (1H, t, J=4.4 Hz), 4.76 (2H, d, J=4.4 Hz), 6.84 (1H, d, J=5.6 Hz), 8.37 (1H, d, J=5.6 Hz).
ESI-MS m/z: 174 (M+H)$^+$.

(4) 3-Chloro-4-methoxy-2-(chloromethyl)pyridine hydrochloride

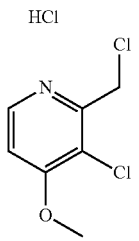

The title compound (558 mg) was obtained as a solid by the same synthesis method as in Example 1(20) using the above (3-chloro-4-methoxypyridin-2-yl)methanol (437 mg).
$^1$H-NMR (CDCl$_3$) δ: 4.26 (3H, s), 5.17 (2H, s), 7.48 (1H, d, J=6.8 Hz), 8.77 (1H, d, J=6.8 Hz).
ESI-MS m/z: 192 (M+H)$^+$.

(5) 4-Amino-2-[(3-chloro-4-methoxypyridin-2-yl)methyl]-N-(2,2-difluoroethyl)-2,7-dihydro-6-thia-1,2,3,5-tetraazabenzo[cd]azulen-8-carboxamide

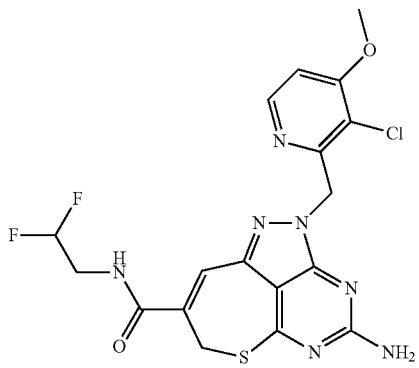

The title compound (48 mg) was obtained as a solid by the same synthesis method as in Example 2(8) using 4-amino-N-(2,2-difluoroethyl)-2,7-dihydro-6-thia-1,2,3,5-tetraazabenzo[cd]azulen-8-carboxamide trifluoroacetate (50 mg) and 3-chloro-2-(chloromethyl)-4-methoxypyridine (35 mg).

$^1$H-NMR (DMSO-D$_6$) δ: 3.55-3.63 (2H, m), 3.96 (3H, s), 4.09 (2H, s), 5.60 (2H, s), 5.95-6.19 (1H, m), 7.06 (2H, brs), 7.16 (1H, d, J=5.73 Hz), 7.49 (1H, s), 8.25 (1H, d, J=5.73 Hz), 8.82 (1H, t, J=5.73 Hz).
ESI-MS m/z, 468 (M+H)$^+$.
Anal. Calcd. For C$_{18}$H$_{16}$ClF$_2$N$_7$O$_2$S.0.25H$_2$O.0.5 dioxane: C, 46.51; H, 4.00; N, 18.99; Cl, 6.86; F, 7.36; S, 6.21.
Found: C, 46.40; H, 3.72; N, 19.10; Cl, 6.93; F, 7.29; S, 6.19.

Example 7

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrobromide A 20% hydrobromic acid-ethanol solution (204 μl, 0.505 mmol) was added to an acetonitrile solution (350 ml) of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (250 mg, 0.561 mmol) at room temperature. The resulting mixture was stirred for 3 hours, and the precipitated solid was then collected by filtration. Ethanol (3 ml) was added to the resulting solid, and the resulting mixture was then stirred for 1 day. Thereafter, the solid was collected by filtration. The solid was then dried under reduced pressure at room temperature for 2 days, so as to obtain the title compound (128 mg, 0.243 mmol).
Anal. Calcd. For C$_{19}$H$_{21}$N$_7$O$_2$SClBr.0.4H$_2$O: C, 42.91; H, 4.01; O, 7.13; N, 18.57; Cl, 6.68; Br, 15.03; S, 6.08.
Found: C, 42.73; H, 4.11; O, 7.19; N, 18.36; Cl, 6.64; Br, 14.96; S, 6.00.

Example 8

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride 3 N hydrochloric acid (0.786 ml, 2.358 mmol) was added to an ethanol (30 ml) suspension of the above 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (527.52 mg, 1.183 mmol), while stirring at 25° C. The resulting mixture was stirred for 1 hour. The precipitated solid was filtered, was washed with ethanol (6 ml), and was then dried under reduced pressure at 40° C. for 30 minutes, so as to obtain the title compound (531.09 mg, 1.101 mmol).
Anal. Calcd. For C$_{19}$H$_{21}$Cl$_2$N$_7$O$_2$S: C, 47.31; H, 4.39; N, 20.33; O, 6.63; Cl, 14.70; S, 6.65.
Found: C, 47.29; H, 4.40; N, 20.02; O, 6.87; Cl, 14.99; S, 6.83.

Example 9

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monomethanesulfonate A diethyl ether solution (50 ml) of methanesulfonic acid (32 mg, 0.302 mmol) was added at 5° C. to an acetonitrile solution (150 ml) of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (151 mg, 0.339 mmol). The resulting mixture was stirred at 5° C. for 25 minutes. Thereafter, the solvent was distilled away under reduced pressure, an appropriate amount of diethyl ether was then added to the residue, and a solid was then collected by filtration. Thereafter, ethanol (1 ml) was added to the resulting solid, and the resulting mixture was then stirred at room temperature for approximately 1 day. Thereafter, a solid was collected by filtration, and it was then dried under reduced pressure at room temperature for 1 day, so as to obtain the title compound (145 mg, 0.268 mmol).

Anal. Calcd. For $C_{20}H_{24}N_7O_5S_2Cl \cdot 0.3H_2O$: C, 44.71; H, 4.69; O, 15.45; N, 17.81; Cl, 6.54; S, 11.56.

Found: C, 43.88; H, 4.53; O, 15.49; N, 17.91; Cl, 6.48; S, 11.71.

Example 10

2-{4-Amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monoethane-1,2-disulfonate An acetone solution (50 ml) of ethane-1,2-disulfonate (70 mg, 0.368 mmol) was added at 5° C. to an acetone solution (50 ml) of 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide (164 mg, 0.368 mmol). The resulting mixture was stirred at 5° C. for 20 minutes. Thereafter, the reaction solution was left at rest at 5° C. for 18 hours, and it was then stirred at room temperature for 7 hours. Thereafter, the precipitated solid was collected by filtration, and it was then dried under reduced pressure at room temperature for approximately 1 day, so as to obtain the title compound (119 mg, 0.187 mmol).

Anal. Calcd. For $C_{21}H_{26}N_7O_8S_3Cl \cdot 1.4H_2O$: C, 38.06; H, 4.68; O, 22.29; N, 14.92; Cl, 5.25; S, 13.83.

Found: C, 38.14; H, 4.39; O, 22.74; N, 14.83; Cl, 5.36; S, 14.55.

Test Example 1

Hsp90 Atpase Assay

An Hsp90 ATPase assay was performed using a recombinant yeast Hsp90 protein (hereinafter called rHsp90). Yeast Hsp90 DNA was cloned from a yeast genomic DNA library according to a conventional method. The cloned yeast Hsp90 DNA was incorporated into a plasmid for expression in *Escherichia coli*, and the plasmid was expressed in *Escherichia coli* to obtain rHsp90.

The test compound was dissolved in DMSO to 10 mM. The dissolved solution was diluted with DMSO to two concentrations, 1 mM and 0.2 mM. Each diluted solution was further 10-fold diluted with an assay buffer (100 mM Tris, pH 7.4, 20 mM KCl, 6 mM $MgCl_2$) (concentration of each test compound solution: 100 µM and 20 µM; DMSO concentration: 10%).

rHsp90 was dissolved in a TE buffer (20 mM Tris, pH 7.4, 1 mM EDTA) to a concentration of 2.531 mg/mL. The solution was diluted with an assay buffer to 125 µg/mL and dispensed to a 96-well assay plate at 40 µL per well (final concentration: 100 µg/mL).

The test compound solution was dispensed at 5 µL per well, and then the solutions in the respective wells were mixed using a plate mixer. 100 mM ATP (Sigma, Catalog No. A-7699) was diluted with an assay buffer to 1 mM and dispensed at 5 µL per well (final concentration: 100 µM). The solutions in the respective wells were mixed using a plate mixer, and then the assay plate was allowed to stand in an incubator set at 37° C. for two hours.

BIOMOL GREEN Reagent (BIOMOL, Catalog No. AK-111) was dispensed at 100 µL per well, and the reaction was terminated. The solutions in the respective wells were mixed using a plate mixer, and then 34% sodium citrate was dispensed at 10 µL per well. The solutions in the respective wells were mixed using a plate mixer, and then the assay plate was left to stand at room temperature for 30 minutes. The absorbance at 650 nm of each well was measured using SpectramaxPLUS (Molecular Devices).

The ratio of the absorbance of the test compound-added group to the absorbance of the test compound-free group (T/C value) was determined by the following calculation formula, based on the assumption that the absorbance of the well to which the test compound and rHsp90 were added was A, the absorbance of the well to which only rHsp90 was added was B, and the absorbance of the well to which neither the test compound nor rHsp90 was added was C. The calculation was carried out using Softmax Pro 4.6 (Molecular Devices). Furthermore, an inhibition rate (%) was calculated using the following calculation formula:

$$T/C=(A-C)/(B-C)$$

The compounds of Examples 1 to 6 each exhibited an ATPase inhibitory activity of 50% or more at a concentration of 2 µM.

Test Example 2

Cell Growth Inhibition Assay

A cell growth inhibition assay was performed using two types of cells (human breast cancer cell line SK-BR-3 and human lung cancer cell line NCI-H460).

Cells of each type were suspended in a medium and seeded into a 96-well multi-well plate at 2000 cells/150 µL/well in the case of SK-BR-3 and at 500 cells/150 µL/well in the case of NCI-H460. The test compound was dissolved in DMSO, and this was diluted with medium to prepare a sample solution (DMSO concentration: 0.5% or less). On the day following the seeding, 50 µL of DMSO-containing medium to which the test compound was not added (hereinafter called DMSO diluted solution; DMSO concentration: 0.5% or less) or 50 µL of the sample solution was further added to the cells. An MTT assay was performed immediately after and 72 hours after adding the sample solution or the DMSO diluted solution to the cells. The MTT assay was performed as follows.

5 mg/mL of an MTT (3-(4,5-dimethylthiazol-2-yl)-2,5-diphenyltetrazolium bromide) solution was added at 20 per well. Thereafter, the plate was incubated at 37° C. in 5% $CO_2$ for four hours. The plate was centrifuged at 1200 rpm for five minutes, and then the culture supernatant was removed by suction using a dispenser. DMSO was added at 150 µL per well, and the generated formazan was dissolved. The plate was stirred using a plate mixer to uniformly color the respective wells. The absorbance of each well was measured using a plate reader at an OD of 540 nm with a reference of 660 nm.

T/C (%) for each concentration was determined by the following calculation formula and a dose-response curve was drawn to calculate the 50% growth inhibitory concentration ($GI_{50}$ value), based on the assumption that the OD value measured immediately after adding the sample solution was S, the OD value measured 72 hours after adding the sample solution was T, and the OD value measured 72 hours after adding the DMSO diluted solution was C.

$$T/C\ (\%) = (T-S)/(C-S) \times 100$$

The results are shown below.

|  | $GI_{50}$ value (nM) | |
| --- | --- | --- |
|  | SK-BR-3 | NCI-H460 |
| Compound 1 | 13 | 26 |
| Compound 2 | 39 | 90 |
| Compound 3 | 14 | 30 |
| Compound 4 | 11 | 22 |
| Compound 5 | 16 | 36 |
| Compound 6 | 45 | 110 |

Test Example 3

In Vivo Antitumor Activity Test

An antitumor activity test was carried out using NCI-H1975 (human non-small cell lung cancer cell line).

On Day 0, the aforementioned cells were subcutaneously transplanted into the right flank region of each male nude mouse ($4 \times 10^6$ cells per mouse).

On Day 10, the body weight and the diameter of tumor were measured. The mice were then randomly divided into groups, such that the groups did not have statistically significant difference in terms of the body weight and the estimated tumor volume (the estimated tumor volume=the long diameter of the tumor×the short diameter of the tumor×the short diameter of the tumor/2).

On Day 11, the diameter of the tumor was measured, and the administration of the test compound was then initiated.

The test compound was prepared to a concentration of 1.5 mg/mL, and it was orally administered to the mice at a dosage of 15 mg/10 mL/kg.

Such administration was carried out once a day during the period from Day 11 to Day 14, and the diameter of the tumor was measured during the period from Day 11 to Day 14 and on Day 17.

On Day 17, the tumor was excised, and the wet weight of the tumor was then measured.

The initial weight of the tumor was calculated from the tumor volume measured on Day 11, defining the gravity as 1.

The increased weight of the tumor was calculated by subtracting the initial weight of the tumor from the wet weight of the tumor measured on Day 17.

The tumor growth inhibition rate (GI %=100−T/C (%)) of each test compound was calculated from the ratio (T/C (%)) of the increased tumor weight (T) of the test compound administration group to the increased tumor weight (C) of the control group (solvent administration group).

The significance test between the control group and the test compound administration group was carried out according to Dunnett's multiple comparison test using EXSAS ver. 7.5.2.2 (Arm Corp).

The compounds of Examples 1 to 6 each exhibited a significant tumor growth inhibitory activity of 50% or more.

Test Example 4

CYP3A4 Inhibition Test Using Human Hepatic Microsome

Midazolam (a substrate; Wako Pure Chemical Industries, Ltd.), 1'-Hydroxymidazolam (a target to be measured; Becton, Dickinson and Company, Japan), Ketoconazole (a positive control; Sigma Chemical Co.), NADPH Regeneration System (Solution A and Solution B (Becton, Dickinson and Company, Japan)) were used. Appropriate amounts of such test compound, substrate, target to be measured, and positive control were weighed. They were dissolved in DMSO, and were then diluted with acetonitrile, as appropriate.

180 µl of a reaction solution prepared by mixing the following (1) to (5) had previously been warmed at 37° C. for 10 minutes:

(1) Potassium phosphate buffer (pH 7.4; final concentration: 50 mM)
(2) Purified water
(3) Midazolam (final concentration: 2.5 µM)
(4) Test compound (final concentration: 10 µM; negative control: no compounds; positive control: Ketoconazole, final concentration: 0.1 µM)
(5) Human hepatic microsome (final concentration: 0.05 mg-P/ml)

20 µl of the NADPH Regeneration System (solution A/solution B/purified water=5/1/4) was added to this reaction solution, and the reaction was initiated. The mixture was incubated for 10 minutes. Thereafter, 50 µl of the reaction solution was sampled, and it was then added to 200 µl of acetonitrile, followed by the termination of the reaction. Further, 50 µl of an acetonitrile solution containing an internal standard substance was added to the reaction solution.

In order to remove proteins from this sample, the reaction solution was transferred to a 96-Well Collection Plate (Waters) using Captiva (registered trademark) (GL Sciences). This sample solution was defined as a sample used for the assay of LC-MS/MS.

Samples of 1'-Hydroxymidazolam having known concentrations (final concentrations: 0 to 5 µM; total 5 points) were prepared, separately. A calibration curve used for assay was prepared, and the concentration of 1'-Hydroxymidazolam in the sample was assayed. This reaction was carried out in a duplicated manner.

The amount of 1'-Hydroxymidazolam generated in the negative control was defined as 100%, and the ratio of the amount of this compound generated by addition of each compound was then calculated. Thus, the inhibition value of CYP3A4 was obtained.

As a result, the inhibition rate of compound 1 was 15%, that of compound 2 was 58%, that of compound 3 was 5%, that of compound 4 was 43%, that of compound 5 was 66%, and that of compound 6 was −18%. The positive control, Ketoconazole, exhibited an inhibition rate of 82%.

Test Example 5

In Vivo Antitumor Activity Test

An antitumor activity test is carried out using NCI-H1650 (human non-small cell lung cancer cell line).

The aforementioned cells are subcutaneously transplanted into the right flank region of each male nude mouse ($1 \times 10^7$ cells per mouse).

Thirty-nine days later, the tumor is excised, and a small section having each side of 2 to 3 mm was prepared. The small section is subcutaneously transplanted into the right flank region of each male nude mouse (Day 0).

On Day 14, the body weight and the diameter of tumor are measured. The mice are then randomly divided into groups, such that the groups do not have statistically significant difference in terms of the body weight and the estimated tumor volume (the estimated tumor volume=the long diameter of the tumor×the short diameter of the tumor×the short diameter of the tumor/2).

On Day 14, the administration of the test compound was then initiated.

The test compounds are prepared to concentrations of 0.65, 0.9, and 1.3 mg/mL, and it is orally administered to the mice at a dosage of 10 mL/kg.

Such administration is carried out once a day during the period from Day 14 to Day 31, and the diameter of the tumor is measured on Day 14, Day 17, Day 21, Day 24, Day 28, and Day 31.

On Day 31, the tumor is excised, and the wet weight of the tumor is then measured.

The initial weight of the tumor is calculated from the tumor volume measured on Day 14, defining the gravity as 1.

The increased weight of the tumor is calculated by subtracting the initial weight of the tumor from the wet weight of the tumor measured on Day 31.

The tumor growth inhibition rate (GI %=100−T/C (%)) of each test compound is calculated from the ratio (T/C (%)) of the increased tumor weight (T) of the test compound administration group to the increased tumor weight (C) of the control group (solvent administration group).

The significance test between the control group and the test compound administration group is carried out according to Dunnett's multiple comparison test using EXSAS ver. 7.5.2.2 (Arm Corp).

The invention claimed is:

1. 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide.

2. A medicament which comprises a compound according to claim 1 or a salt thereof as an active ingredient.

3. A pharmaceutical composition which comprises a compound according to claim 1 or a salt thereof and a pharmacologically acceptable carrier.

4. A method for treating breast or lung cancer which comprises administering a compound according to claim 1 or a salt thereof.

5. A method for treating breast or lung cancer according to claim 4, wherein the breast or lung cancer involves the excessive expression of an HSP90 client protein(s).

6. A method for treating breast or lung cancer according to claim 4, wherein the breast or lung cancer involves the mutation of an HSP90 client protein(s).

7. A method for treating breast or lung cancer according to claim 4, wherein the breast or lung cancer involves the activation of an HSP90 client protein(s).

8. A method for treating breast or lung cancer according to claim 4, wherein the breast or lung cancer involves the activation of an intracellular signalling pathway to which an HSP90 client protein(s) belongs.

9. A method for treating breast or lung cancer according to claim 4, wherein the breast or lung cancer is dependent on an HSP90 client protein(s).

10. 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrobromide.

11. 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monohydrochloride.

12. 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monoethanesulfonate.

13. 2-{4-amino-2-[(3-chloro-4-methoxy-5-methylpyridin-2-yl)methyl]-2,7-dihydro-6-thia-1,2,3,5-tetraazabenzo[cd]azulen-8-yl}-N-methylacetamide monoethane-1,2-disulfonate.

14. A pharmaceutical composition which comprises the salt according to claim 10 and a pharmacologically acceptable carrier.

15. A method for treating breast or lung cancer which comprises administering the salt according to claim 10.

16. A method for treating breast or lung cancer according to claim 15, wherein the breast or lung cancer involves the excessive expression of an HSP90 client protein(s).

17. A method for treating breast or lung cancer according to claim 15, wherein the breast or lung cancer involves the mutation of an HSP90 client protein(s).

18. A method for treating breast or lung cancer according to claim 15, wherein the breast or lung cancer involves the activation of an HSP90 client protein(s).

19. A method for treating breast or lung cancer according to claim 15, wherein the breast or lung cancer involves the activation of an intracellular signalling pathway to which an HSP90 client protein(s) belongs.

20. A method for treating breast or lung cancer according to claim 15, wherein the breast or lung cancer is dependent on an HSP90 client protein(s).

21. A pharmaceutical composition which comprises the salt according to claim 11 and a pharmacologically acceptable carrier.

22. A method for treating breast or lung cancer which comprises administering the salt according to claim 11.

23. A method for treating breast or lung cancer according to claim 22, wherein the breast or lung cancer involves the excessive expression of an HSP90 client protein(s).

24. A method for treating breast or lung cancer according to claim 22, wherein the breast or lung cancer involves the mutation of an HSP90 client protein(s).

25. A method for treating breast or lung cancer according to claim 22, wherein the breast or lung cancer involves the activation of an HSP90 client protein(s).

26. A method for treating breast or lung cancer according to claim 22, wherein the breast or lung cancer involves the activation of an intracellular signalling pathway to which an HSP90 client protein(s) belongs.

27. A method for treating breast or lung cancer according to claim 22, wherein the breast or lung cancer is dependent on an HSP90 client protein(s).

28. A pharmaceutical composition which comprises the salt according to claim 12 and a pharmacologically acceptable carrier.

29. A method for treating breast or lung cancer which comprises administering the salt according to claim 12.

30. A method for treating breast or lung cancer according to claim 29, wherein the breast or lung cancer involves the excessive expression of an HSP90 client protein(s).

31. A method for treating breast or lung cancer according to claim 29, wherein the breast or lung cancer involves the mutation of an HSP90 client protein(s).

32. A method for treating breast or lung cancer according to claim 29, wherein the breast or lung cancer involves the activation of an HSP90 client protein(s).

33. A method for treating breast or lung cancer according to claim 29, wherein the breast or lung cancer involves the activation of an intracellular signalling pathway to which an HSP90 client protein(s) belongs.

34. A method for treating breast or lung cancer according to claim 29, wherein the breast or lung cancer is dependent on an HSP90 client protein(s).

35. A pharmaceutical composition which comprises the salt according to claim 13 and a pharmacologically acceptable carrier.

36. A method for treating breast or lung cancer which comprises administering the salt according to claim 13.

37. A method for treating breast or lung cancer according to claim 36, wherein the breast or lung cancer involves the excessive expression of an HSP90 client protein(s).

38. A method for treating breast or lung cancer according to claim 36, wherein the breast or lung cancer involves the mutation of an HSP90 client protein(s).

39. A method for treating breast or lung cancer according to claim 36, wherein the breast or lung cancer involves the activation of an HSP90 client protein(s).

40. A method for treating breast or lung cancer according to claim 36, wherein the breast or lung cancer involves the activation of an intracellular signalling pathway to which an HSP90 client protein(s) belongs.

41. A method for treating breast or lung cancer according to claim 36, wherein the breast or lung cancer is dependent on an HSP90 client protein(s).

* * * * *